US006218110B1

(12) United States Patent
Nakayama et al.

(10) Patent No.: US 6,218,110 B1
(45) Date of Patent: Apr. 17, 2001

(54) **OLIGONUCLEOTIDES FOR DETECTING VEROTOXIN-PRODUCING *E. COLI* AND DETECTION PROCESS**

(75) Inventors: Tomoko Nakayama, Osaka; Jun Tada, Muko; Shigeru Fukushima, Otsu; Tetsuo Ohashi, Kyoto, all of (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 08/968,046

(22) Filed: Nov. 12, 1997

Related U.S. Application Data

(62) Division of application No. 08/328,710, filed on Oct. 25, 1994, now Pat. No. 5,795,717.

(30) Foreign Application Priority Data

Feb. 28, 1994 (JP) ...................................... 6-30277
Mar. 18, 1994 (JP) ...................................... 6-48174

(51) Int. Cl.$^7$ .............................. C12Q 1/68; C12P 19/34; C07H 21/04
(52) U.S. Cl. .......................... 435/6; 435/91.2; 536/24.31; 536/24.33
(58) Field of Search .................... 435/6, 91.2; 536/24.33, 536/24.32

(56) References Cited

U.S. PATENT DOCUMENTS 4,683,195 * 7/1987 Mullis et al. ............................ 435/6

FOREIGN PATENT DOCUMENTS

| 0355989 | 2/1990 | (EP) . |
| 0409159 | 1/1991 | (EP) . |
| 0526876 | 2/1993 | (EP) . |

OTHER PUBLICATIONS

Lin et al. Microbiol. & Immunol. (1993) 37(6):451–459.*
Lin et al. Microbiol. & Immunol. (1993) 37(7):543–548.*
Woodward et al. Veterinary Microbiol (1992) 31: 251–261.*
Strockbine et al. J. Bacteriol. (1988) 170(3):1116–1122.*
O. Sethabutr et al., The Journal of Infectious Diseases, Detection of Shigellae and Enteroinvasive . . . , vol. 167, No. 2, Feb. 1993, pp. 458–461.
D.R. Pollard et al., Journal of Clinical Microbiology, Rapid and Specific . . . , vol. 28, No. 3, Mar. 1990, pp. 540–545.
K.A. Lampel et al., Applied and Environmental Microbiology, Polymerase Chain Reaction . . . , vol. 56, No. 6, Jun. 1990, pp. 1536–1540.
D.R. Pollard et al., The Journal of Infectious Diseases, Differentiation of Shiga . . . , vol. 162, No. 5, Nov. 1990, pp. 1195–1198.

Database WPI, Week 9514, Derwent Publications Ltd., London, GB; AN 95–100815 & JP–A–07 008280, Jan. 13, 1995, Abstract.
Database WPI, Week 9202, Derwent Publications Ltd., London, GB; AN 92–012715 & JP–A–03 262 500, Nov. 22, 1991, Abstract.
M.P. Jackson, Journal of Clinical Microbiology, Detection of Shiga Toxin–Producing Shigella . . . , vol. 29, No. 9, Sep. 1991, pp. 1910–1914.
Database WPI, Week 9249, Derwent Publications Ltd., London, GB: AN 92–401805 & JP–A–04 297 488, Oct. 21, 1992, Abstract.
Database WPI, Week 9249, Derwent Publications Ltd., London, GB; AN 92–401806 & JP–A–04 297 489, Oct. 21, 1992, Abstract.
Database WPI, Week 9347, Derwent Publications Ltd., London, GB; AN 93–373605 & JP–A–05 276 996, Mar. 31, 1992, Abstract.
Patent Abstracts of Japan, vol. 16, No. 338, Jul. 22, 1992 & JP–A–04 099488, Mar. 31, 1992, Abstract.
Patent Abstracts of Japan, vol. 15, No. 193, May 17, 1991 & JP–A–03 049699, Mar. 4, 1991.
Database WPI, Week 9428, Derwent Publications Ltd., London, GB; AN 94–230239, & JP–A–06 165 698, Jun. 14, 1994, Abstract.
Database WPI, Week 9503, Derwent Publications Ltd., London, GB: AN 95–018273, & JP–A–06 303 976, Nov. 1, 1994, Abstract.
Innis and Gelfand, In PCR Protocols: A Guide to Methods and Technology, Academic Press, 1990, Chapter 1.
Database WPI, Week 9514, Derwent Publications Ltd., London, GB; AN 95–100814 & JP–A–07 008279, Jan. 13, 1995, Abstract.

* cited by examiner

Primary Examiner—Lisa B. Arthur
(74) Attorney, Agent, or Firm—Birch, Stewart, Kolasch & Birch LLP

(57) ABSTRACT

A synthetic oligonucleotide which is complementary to a nucleotide sequence of a gene selected from the group consisting of the Shiga toxin gene of Shigella species, the ipaH gene of Shigella species and EIEC, the invE gene of Shigella species and EIEC, the araC gene of Salmonella species, the Verocytotoxin-1 gene of EHEC or VTEC, the Verocytotoxin-2 gene of EHEC or VTEC, the toxic shock syndrome toxin-1 gene of *Staphylococcus aureus*, the ctx gene of *Vibrio cholerae*, and the enterotoxin gene of *Clostridium perfringens*; a method for detecting a bacterial strain by amplifying a region of the above gene by PCR using the above oligonucleotides as primers and detecting the amplified region; and a kit for the detection of the bacterial strain.

5 Claims, 4 Drawing Sheets

OLIGONUCLEOTIDES FOR DETECTING VEROTOXIN-PRODUCING E. COLI AND DETECTION PROCESS

This application is a divisional of application Ser. No. 08/328,710, filed on Oct. 25, 1994, now U.S. Pat. No. 5,795,717 the entire contents of which are hereby incorporated by reference.

BACKGROUND OF THE INVENTION

1. Field of the Invention

The present invention relates to detection of pathogenic bacteria in samples (e.g., clinical isolates and food specimens) for the purposes of diagnoses, screenings, quarantine inspections, and clinical tests. Specifically, it relates to detection of pathogens associated with bacterial food poisoning and bacterial diarrhea. More specifically, it relates to detection of enteropathogenic bacteria including Shigella species, Salmonella species, enterohemorrhagic *Escherichia coli* or Verocytotoxin-producing *Escherichia coli*, *Staphylococcus aureus*, *Vibrio cholerae*, and *Clostridium perfringens*.

2. Discussion of the Related Art

Detection of pathogenic bacteria such as Shigella species, Salmonella species, enterohemorrhagic *Escherichia coli* (hereinafter simply referred to as EHEC) or Verocytotoxin-producing *Escherichia coli* (hereinafter simply referred to as VTEC), *Staphylococcus aureus*, *Vibrio cholerae*, and *Clostridium perfringens* is an important task in the field of medicine and public hygiene, and various methods have been used.

Conventionally, detection of a pathogenic bacterial strain involves isolation of several pathogenic bacterial colonies and identification of the species of the bacteria by serological or biochemical method.

In the case of Shigella species, this has been achieved by culturing and isolating the target bacterium from specimens of patient stools, food, or the like, using a medium, such as DHL agar or MacConkey's agar, and then further culturing the bacterium using a medium such as TSI agar or LIM agar for the purpose of identification.

In the case of Salmonella species, culture is conducted for isolation of the bacteria from specimens of patient stools or vomits, food or wiping samples, etc., followed by inoculation to TSI agar, SIM medium, VP-MR medium and lysine decarboxylation test medium and subsequent overnight culture at 37° C., to confirm Salmonella species, and the serotype is determined using a commercially available set of antisera against O and H antigens.

EHEC or VTEC has been found to cause hemolytic uremic syndrome in children, as well as food poisoning symptoms, typically hemorrhagic colitis, and stress has recently been placed on detection of this bacterium in clinical tests. In the case of detecting EHEC or VTEC, specimens are patient stools, food, or water samples (drinking water, river water, etc.) collected from the environment surrounding the patient. In detecting EHEC (VTEC) in these specimens, it is necessary to perform a series of procedures from direct isolation culture, a primary confirmation culture test, and a secondary confirmation culture test to an agglutination test with an antiserum.

In the case of *Staphylococcus aureus*, specimens are patient vomits or stools, food the patient ate, samples wiped out from the environment surrounding the patient, or the like. Before *Staphylococcus aureus* is detected and identified in these specimens, it is necessary to perform bacterial culture, isolation culture and then pure culture and confirmation culture.

In the case of *Vibrio cholerae*, specimens are patient stools or food, or water samples (drinking water, river water, sea water, etc.) or benthos samples collected from the environment surrounding the patient. In detecting and identifying *Vibrio cholerae* in these specimens, it is necessary to perform a series of procedures from primary enrichment culture, secondary enrichment culture, and isolation culture to an agglutination reaction test with anti-*V. cholerae* 01 serum and confirmation culture.

In the case of *Clostridium perfringens*, specimens are obtained mainly from patient stools and food. For detection and identification, the specimens are subjected to enrichment culture and isolation culture under anaerobic conditions. With several colonies of the bacteria, tests for biochemical properties are conducted.

Any identification process mentioned above usually takes several days, and hampers rapid diagnoses of infectious diseases.

Specifically, in the case of Shigella species, each culture step takes 18–24 hours, totalling 3–4 days; rapid detection is difficult. Other available methods include the reversed passive latex agglutination using a specific antibody to the Shiga toxin, the EIA method using a specific antibody to the 140 MDal plasmid product associated with the pathogenicity of Shigella species and enteroinvasive *Escherichia coli* [Kenichiro Ito et al., Japanese Journal of Bacteriology 41, 414 (1986)] and the DNA probe method for detecting the ipaB gene, the ipac gene, or the ipaD gene (U.S. patent application No. 888,194). However, these testing methods require complicated troublesome procedures in preparing reagents and specimens, and take much time.

In the case of Salmonella species, 2–3 days are taken for bacterial isolation and identification of the bacteria from specimens. In addition, Salmonella tests are difficult to conduct in ordinary laboratories, because as many as 100 antisera and much experience are required to achieve complete serum typing of Salmonella species, which involve a large number of serum types. Also, each culture step and serotyping test take 3–4 days; rapidity is poor. Moreover, confirmation culture and serotyping are expensive and involve troublesome operation.

In the case of EHEC (VTEC), each culture step takes 18–24 hours, totalling as many as 3–4 days. The currently representative serotype of EHEC (VTEC) is 0157:H7, but no diagnostic antiserum has been commercially available for identification of this serotype, so that the diagnostic antiserum has to be prepared by the investigator. In addition, it is often difficult to identify the causative bacterium solely on the basis of serum typing in EHEC (VTEC), because the serum type and the pathogenicity do not always agree with each other. Therefore, the conventional testing method for EHEC (VTEC) lacks rapidity and simplicity, and is not suitable for practical application.

In the case of *Staphylococcus aureus*, each culture step takes 18–24 hours, totalling as many as about 4 days when combined with the time required for the subsequent testings. Also, in the biochemical test in culture for identification, various properties, such as aerobic growth, VP reactivity, nitrate reduction, Tween 80 hydrolyzability, hyaluronidase activity and sugar decomposition, should be examined, but this process is troublesome, tedious and expensive. The most reliable method for identifying the causative bacterium for food poisoning and diarrhea is to test the isolated strain for exotoxin (toxic shock syndrome toxin-1, hereinafter simply referred to as TSST-1) production. However, even when a commercially available convenient reagent kit is used, 18–20 hours will be taken to obtain the results; rapidity is poor.

In the case of *Vibrio cholerae*, each culture step takes 18–24 hours, totalling as many as about 4 days. In the biochemical test concerning confirmation culture, various properties, such as oxidase test positivity, indole test positivity, motility, and lysine decarboxylation test positivity should be examined. These tests are troublesome, tedious and expensive, and the results obtained are difficult to assess in some cases. Moreover, in the case of *Vibrio cholerae*, it is essential to test the isolated strain for enterotoxin (cholera toxin; CT) production to take an administrative measure for pest control. However, even when a commercially available convenient reagent kit is used, 18–20 hours will be taken to obtain the results; rapidity is poor and practical applicability is low.

In the case of Welch's bacillus(*Clostridium perfringens*), the detection requires considerably long time: each culture step takes 18–48 hours, totalling 5–6 days. In addition, since *Clostridium perfringens* strains are widely distributed in the nature, only the detection of the bacterial strain from specimens is not enough to determine the strain as the causative agent for food poisoning. Further tests are required, including detection of the enterotoxin in patient stool, assay of the isolated strain for enterotoxin production, serotype determination, and bacterial count for suspected food. These procedures consume much time and labor, and lack rapidity and simplicity.

In recent years, the DNA probing or hybridization using oligonucleotides has been tried. However, when hybridization is performed on a membrane or on other supports using a probe of a labeled oligonucleotide, followed by detection of the probe, sensitivity of the assays depends on numbers of organisms available for detection. Therefore it is difficult to achieve a high detection sensitivity and selectivity in this test without the above-described pretreatment of the separation culture.

SUMMARY OF THE INVENTION

It is object of the present invention to provide synthetic oligonucleotides used as primers for PCR to amplify certain regions of the genes specific to the above various pathogenic microorganisums.

It is another object of the present invention to provide a simple, rapid and highly sensitive process for detecting the above various pathogenic microorganisms for quarantine inspection, clinical laboratory examination and food inspection, wherein a region of a gene specific to the bacterial strain to be detected is amplified by the PCR technique using synthetic oligonucleotide primers.

It is still another object of the present invention to provide a kit for detection of the above various bacterial strains, comprising at least a pair of primers, a thermostable DNA polymerase, and dNTP solutions.

The gist of the present invention relates to:
1) A synthetic oligonucleotide of 10 to 30 bases which is complementary to a nucleotide sequence of a gene selected from the group consisting of the Shiga toxin gene of Shigella species, the ipaH gene of Shigella species and enteroinvasive *Escherichia coli* (hereinafter simply referred to as EIEC), the invE gene of Shigella species and EIEC, the araC gene of Salmonella species, the Verocytotoxin-1 gene of EHEC or VTEC, the Verocytotoxin-2 gene of EHEC or VTEC, the toxic shock syndrome toxin gene of *Staphylococcus aureus*, the ctx gene of *Vibrio cholerae*, and the enterotoxin gene of *Clostridium perfringens*;
2) A synthetic oligonucleotide comprising a nucleotide sequence complementary to the synthetic oligonucleotide of 1);
3) A method for detecting a bacterial strain selected from the group consisting of Shigella species, EIEC, Salmonella species, EHEC, VTEC, *Staphylococcus aureus, Vibrio cholerae* and *Clostridium perfringens*, wherein the method comprises:

(1) hybridizing one primer to a single-stranded target DNA as a template DNA present in a specimen and carrying out a primer extension reaction to give a primer extension product, (2) denaturing the resulting DNA duplex to separate the primer extension product from the template DNA; the primer extension product functioning as the other template DNA for the other primer, (3) repeating a cycle of simultaneous primer extension reaction with the two primers, separation of the primer extension products from the templates, and hybridization of primers to amplify a region of the target DNA, in the steps from (1) to (3), the primers being selected from the group consisting of oligonucleotides of 1) and 2), (4) detecting the amplified nucleotide sequence to determine whether a suspected bacterial strain is present in the specimen; and 4) A kit for detection of a bacterial strain, comprising at least a pair of primers selected from the group consisting of oligonucleotides of 1) and 2), a thermostable DNA polymerase, and dNTP solutions.

The present invention provides a highly selective and highly sensitive method for rapid detection of Shigella species having the Shiga toxin gene, the ipaH gene and the invE gene, EIEC having the ipah gene and the invE gene, Salmonella species having the araC gene, EHEC having the VT1 gene and the VT2 gene, *Staphylococcus aureus* having the TSST-1 gene, *Vibrio cholerae* having the ctx gene, and *Clostridium perfringens* having the enterotoxin gene.

BRIEF DESCRIPTION OF THE DRAWINGS

The present invention will become more fully understood from the detailed description given hereinbelow and the accompanying drawings which are given by way of illustration only, and thus, are not limitative of the present invention.

Lanes 1 to 3: *Vibrio cholerae* (El Tor—Ogawa type, the ctx gene positive strain)

Lanes 4 to 6: *Vibrio cholerae* (El Tor—Inaba type, the ctx gene positive strain)
Lane 7: *Vibrio cholerae* (Classical—Ogawa type, the ctx gene positive strain)
Lane 8: *Vibrio cholerae* (Classical—Inaba type, the ctx gene positive strain)
Lanes 9 to 10: *Vibrio cholerae* (non-O1, the ctx gene positive strain)
Lane 11: *Vibrio cholerae* (El Tor—Ogawa type, the ctx gene negative strain)
Lane 12: *Vibrio cholerae* (El Tor—Inaba type, the ctx gene negative strain)
Lane 13: Enterotoxigenic *Escherichia coli*(Thermolabile enterotoxin gene positive strain).

Figure 3:
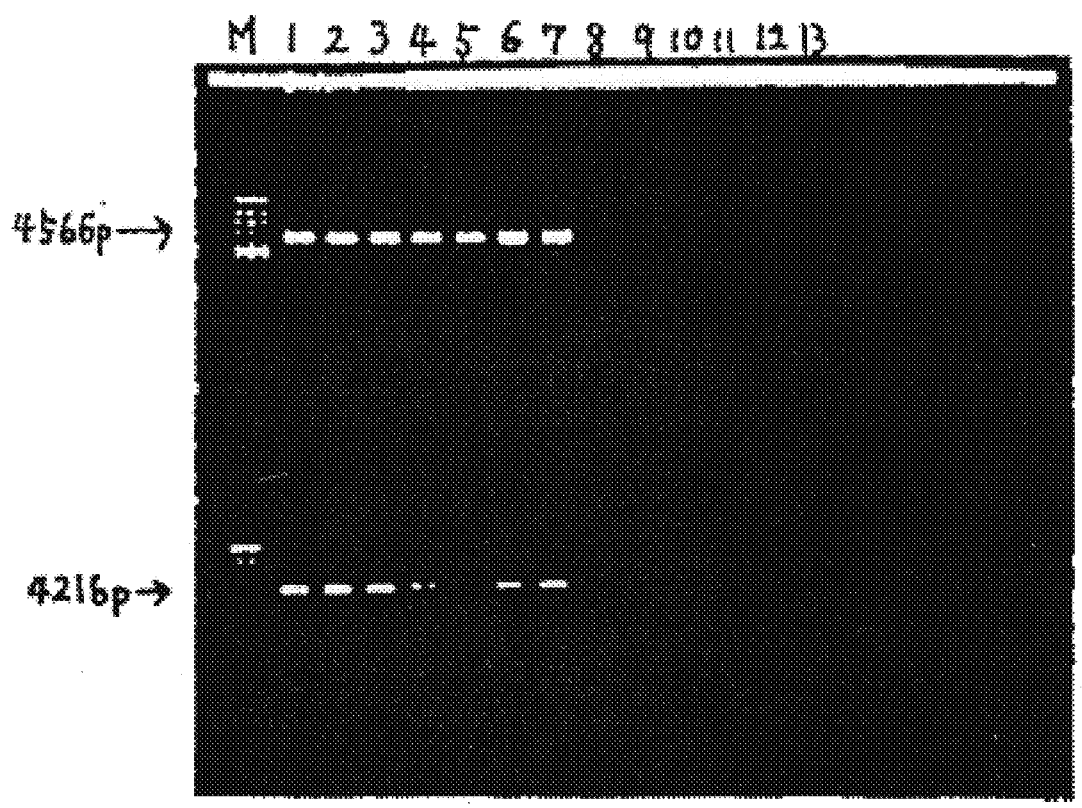

FIG. 3 is the electrophoretic pattern of the agarose gel electrophoresis for the nucleotide fragments amplified by PCR to detect the enterotoxin gene of *Clostridium perfringens*, the upper part being the results obtained with Oligonucleotide SEQ ID NO:28+Oligonucleotide SEQ ID NO:33; the lower part being the results obtained with Oligonucleotide SEQ ID NO:29+Oligonucleotide SEQ ID NO:33, wherein M indicates the molecular weight marker and lanes 1–13 indicate the template DNA derived from heat extracts of the following strains: Lane 1, ATCC 12925; Lane 2, ATCC 12924; Lane 3, ATCC 12922; Lane 4, ATCC 12920; Lane 5, ATCC 12916; Lane 6, ATCC 12915; Lane 7, ATCC 12918; Lane 8, ATCC 12919; Lane 9, ATCC 12921; Lane 10, JCM 1296; Lane 11, JCM 1416; Lane 12, JCM 1382; and Lane 13, negative control.

Figure 4:
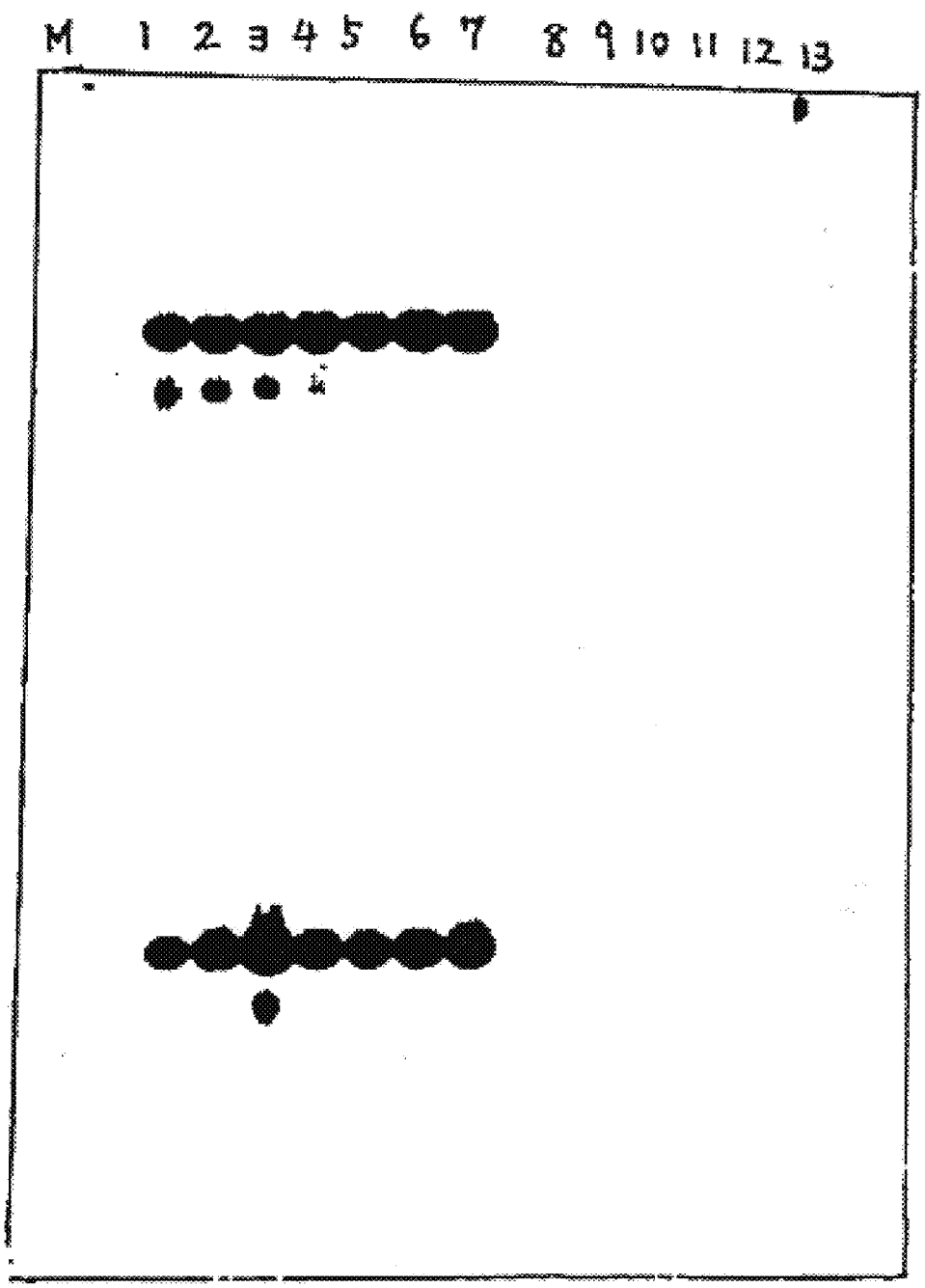

FIG. 4 shows the results of a Southern blot hybridization test to confirm if the nucleotide sequence of amplified DNA with the primers of the present invention is a part of the enterotoxin gene sequences of *Clostridium perfringens*, the upper part being the results obtained with Oligonucleotide SEQ ID NO:28+Oligonucleotide SEQ ID NO:33; the lower part being the results obtained with Oligonucleotide SEQ ID NO:29+Oligonucleotide SEQ ID NO:33, wherein M indicates the molecular weight marker and lanes 1–13 indicate the template DNA solutions derived from heat extracts of the following strains: Lane 1, ATCC 12925; Lane 2, ATCC 12924; Lane 3, ATCC 12922; Lane 4, ATCC 12920; Lane 5, ATCC 12916; Lane 6, ATCC 12915; Lane 7, ATCC 12918; Lane 8, ATCC 12919; Lane 9, ATCC 12921; Lane 10, JCM 1296; Lane 11, JCM 1416; Lane 12, JCM 1382; and Lane 13, negative control.

DETAILED DESCRIPTION OF THE INVENTION

Oligonucleotides

An oligonucleotide of the present invention is a synthetic oligonucleotide which complementarily and selectively hybridizes to a gene specific to a pathogenic bacterial strain such as Shigella species, EIEC, Salmonella species, EHEC or VTEC, *Staphylococcus aureus, Vibrio cholerae*, and *Clostridium perfringens*. In the bacterial detection of the present invention, the oligonucleotides are used as primers in the PCR to amplify a DNA sequence of a target gene specific to the pathogenic bacteria to be detected. For this purpose, any combination of two oligonucleotides of the present invention may optionally be employed without particular limitation as long as a DNA sequence of 50 to 2000 bases, preferably of 100 to 1000 bases, can be amplified. The preferred combination of oligonucleotides are described in detail in the following preferred embodiments.

In the oligonucleotides mentioned below, T may be replaced with U without impairing the advantageous effect of the oligonucleotide.

Preferred Embodiment 1:

For the detection of Shigella species (*Shigella dysenteriae, Shigella flexneri, Shigella boydii* and *Shigella sonnei*) and EIEC, the Shiga toxin gene specific to Shigella species, the ipah gene specific to Shigella species and EIEC, or the invE gene specific to Shigella species and EIEC is selected as the target gene.

When the Shiga toxin gene is targeted, two oligonucleotides, one comprising at least 10 consecutive bases of the following oligonucleotide SEQ ID No.1 and the other comprising at least 10 consecutive bases of the following oligonucleotide SEQ ID NO: 2, are selected in the present invention:

(5')-CAACACTGGATGATCTCAG-(3') (SEQ ID NO: 1)
(5')-CCCCCTCAACTGCTAATA-(3') (SEQ ID NO: 2)

When the ipah gene is targeted, two oligonucleotides, one comprising at least 10 consecutive bases of oligonucleotide SEQ ID NO:3 and the other comprising at least 10 consecutive bases of oligonucleotide SEQ ID NO:4 are selected in the present invention:

(5')-TGTATCACAGATATGGCATGC-(3') (SEQ ID NO:3)
(5')-TCCGGAGATTGTTCCATGTG-(3') (SEQ ID NO:4)

When the invE gene is targeted, two oligonucleotides, one comprising at least 10 consecutive bases of oligonucleotide SEQ ID NO:5 and the other comprising at least 10 consecutive bases of oligonucleotide SEQ ID NO:6 are selected in the present invention:

(5')-CAAGATTTAACCTTCGTCAACC-(3') (SEQ ID NO:5)
(5')-AGTTCTCGGATGCTATGCTC-(3') (SEQ ID NO:6)

Preferred Embodiment 2:

For the detection of Salmonella species, the araC gene is targeted.

For this purpose, any one of the following oligonucleotide combinations is preferably selected in the present invention: a combination in which one oligonucleotide comprises at least 10 consecutive bases of oligonucleotide SEQ ID NO:7 and the other comprises at least 10 consecutive bases of oligonucleotide SEQ ID NO:8; a combitnation in which one comprises at least 10 consecutive bases of oligonucleotide SEQ ID NO:9 and the other comprises at least 10 consecutive bases of oligonucleotide SEQ ID NO:10; and a combination in which one comprises at least 10 consecutive bases of oligonucleotide SEQ ID NO: 11 and the other comprises at least 10 consecutive bases of oligonucleotide SEQ ID NO: 8:

(5')-CGCGGAGAGGGCGTCATT-(3') (SEQ ID NO:7)
(5')-GCAACGACTCATTAATTACCG-(3') (SEQ ID NO:8)
(5')-ATCTGGTCGCCGGGCTGA-(3') (SEQ ID NO:9)
(5')-GCATCGCGCACACGGCTA-(3') (SEQ ID NO:10)
(5')-GGCGAGCAGTTTGTCTGTC-(3') (SEQ ID NO:11)

Preferred Embodiment 3:

For the detection of EHEC or VTEC strains, the Verocytotoxin-1 (VT1) gene or the Verocytotoxin-2 (VT2) gene is targeted.

In order to detect bacteria which have only the VT1 gene, two oligonucleotides, one comprising at least 10 consecutive bases of oligonucleotide SEQ ID NO:12 and the other comprising at least 10 consecutive bases of oligonucleotide SEQ ID NO:13, are preferably selected in the present invention:

(5')-CAACACTGGATGATCTCAG-(3') (SEQ ID NO:12)

(5')-CCCCCTCAACTGCTAATA-(3') (SEQ ID NO:13)

In order to detect bacteria which have only the VT2 gene or its variant genes (VT2vha, VT2vhb and VT2vp1), two oligonucleotides, one comprising at least 10 consecutive bases of oligonucleotide SEQ ID NO:14 and the other comprising at least 10 consecutive bases of oligonucleotide SEQ ID NO:15, are preferably selected in the present invention:

(5')-ATCAGTCGTCACTCACTGGT-(3') (SEQ ID NO:14)

(5')-CCAGTTATCTGACATTCTG-(3') (SEQ ID NO:15)

In order to detect bacteria which have both the VT1 gene and the VT2 gene (including the VT2vha, VT2vhb and VT2vp1 genes), any one of the following oligonucleotide combinations is preferably selected in the present invention: a combination in which one oligonucleotide comprises at least 10 consecutive bases of oligonucleotide SEQ ID NO:16 and the other comprises at least 10 consecutive bases of oligonucleotide SEQ ID NO:18; and a combination in which one comprises at least 10 consecutive bases of oligonucleotide SEQ ID NO:17 and the other comprises at least 10 consecutive bases of oligonucleotide SEQ ID NO:18:

(5')-AGTTTACGTTAGACTTTTCGAC-(3') (SEQ ID NO:16)

(5')-CGGACAGTAGTTATACCAC-(3') (SEQ ID NO:17)

(5')-CTGCTGTCACAGTGACAAA-(3') (SEQ ID NO:18)

Preferred Embodiment 4:

For the detection of *Staphylococcus aureus*, the TSST-1 gene is targeted.

For this purpose, any one of the following oligonucleotide combination is preferably selected in the present invention: a combination in which one oligonucleotide comprises at least 10 consecutive bases of oligonucleotide SEQ ID NO:20 and the other comprises at least 10 consecutive bases of oligonucleotide SEQ ID NO:21; a combination in which one comprises at least 10 consecutive bases of oligonucleotide SEQ ID NO:19 and the other comprises at least 10 consecutive bases of oligonucleotide SEQ ID NO:22; and a combination in which one comprises at least 10 consecutive bases of oligonucleotide SEQ ID NO: 20 and the other comprises at least 10 consecutive bases of oligonucleotide SEQ ID NO: 22:

(5')-CCTTTAAAAGTTAAGGTTCATG-(3') (SEQ ID NO:19)

(5')-GGCCAAAGTTCGATAAAAAAC-(3') (SEQ ID NO:20)

(5')-ATTTATAGGTGGTTTTTCAGTAT-(3') (SEQ ID NO:21)

(5')-CTGCTTCTATAGTTTTTATTTCA-(3') (SEQ ID NO:22)

Preferred Embodiment 5:

For the detection of *Vibrio cholerae*, the ctx gene is targeted.

For this purpose, any one of the following oligonucleotide combinations is preferably selected in the present invention: a combination in which one oligonucleotide comprises at least 10 consecutive bases of oligonucleotide SEQ ID NO:23 and the other comprises at least 10 consecutive bases of oligonucleotide SEQ ID NO:25; and a combination in which one comprises at least 10 consecutive bases of oligonucleotide SEQ ID NO:24 and the other comprises at least 10 consecutive bases of oligonucleotide SEQ ID NO:26:

(5')-TGATGAAATAAAGCAGTCAGGT-(3') (SEQ ID NO:23)

(5')-ACAGAGTGAGTACTTTGACC-(3') (SEQ ID NO:24)

(5')-GGCACTTCTCAAACTAATTGAG-(3') (SEQ ID NO:25)

(5')-ATACCATCCATATATTTGGGAG-(3') (SEQ ID NO:26)

Preferred Embodiment 6:

For the detection of *Clostridium perfringens*, the enterotoxin gene is targeted.

For this purpose, any one of the following oligonucleotide combinations is preferably selected in the present invention: a combination in which one oligonucleotide comprises at least 10 consecutive bases of oligonucleotide SEQ ID NO:27 and the other comprises at least 10 consecutive bases of oligonucleotide SEQ ID NO:32; a combination in which one comprises at least 10 consecutive bases of oligonucleotide SEQ ID NO:28 and the other comprises at least 10 consecutive bases of oligonucleotide SEQ ID NO:33; a combination in which one comprises at least 10 consecutive bases of oligonucleotide SEQ ID NO:29 and the other comprises at least 10 consecutive bases of oligonucleotide SEQ ID NO:33; a combination in which one comprises at least 10 consecutive bases of oligonucleotide SEQ ID NO:30 and the other comprises at least 10 consecutive bases of oligonucleotide SEQ ID NO:34; and a combination in which one comprises at least 10 consecutive bases of oligonucleotide SEQ ID NO:31 and the other comprises at least 10 consecutive bases of oligonucleotide SEQ ID NO:35:

(5')-TCTGAGGATTTAAAAACACC-(3') (SEQ ID NO:27)

(5')-ACCCTCAGTAGGTTCAAGTC-(3') (SEQ ID NO:28)

(5')-ATGAAACAGGTACCTTTAGCC-(3') (SEQ ID NO:29)

(5')-GGTAATATCTCTGATGATGGAT-(3') (SEQ ID NO:30)

(5')-TAACTCATACCCTTGGACTC-(3') (SEQ ID NO:31)

(5')-GAACCTTGATCAATATTTCC-(3') (SEQ ID NO:32)

(5')-GTAGCAGCAGCTAAATCAAGG-(3') (SEQ ID NO:33)

(5')-AGTCCAAGGGTATGAGTTAG-(3') (SEQ ID NO:34)

(5')-CCATCACCTAAGGACTGTTC-(3') (SEQ ID NO:35)

Amplification of Gene Sequence by PCR

For amplification of a region of a target gene in the present invention, the PCR developed by Saiki et al. [Science 230, 1350 (1985)] is employed.

Specifically, two oligonucleotide primers that flank a specific region of a target gene (in the present invention, the Shiga toxin gene of Shigella species, the ipaH and invE genes of Shigella species and EIEC, the araC gene of Salmonella species, the VT1 and VT2 genes of EHEC or VTEC, the TSST-1 gene of *Staphylococcus aureus*, the ctx gene of *Vibrio cholerae* and the enterotoxin gene of *Clostridium perfringens*) are synthesized.

In PCR, one of the oligonucleotide primers selectively hybridizes to the (+)-strand of a target gene DNA, and the other hybridizes to the (−)-strand of the DNA. Then, both the oligonucleotides serve as primers of template dependent DNA polymerization respectively. In the present invention, single strand DNAs formed by heat denaturation of double strand DNAs in specimens are used as templates. The duplexes resulting from the DNA polymerization reaction are then denatured to separate the primer extension products from the templates. Then, the primer extension products themselves serve as the templates for the next DNA polymerization reaction. The cycle of denaturation, primer annealing in which a primer hybridizes with a template DNA and a primer extension reaction is repeated until the region of the target gene is amplified enough for its detection.

Specimens applicable to the PCR in the present invention may include clinical samples such as stool, urine, blood, tissue homogenate, and food samples. A specimen for PCR should be pre-treated to release the nucleic acid components from the bacterial cells present therein. Since PCR can be carried out with only several to several tens of nucleic acid molecules, a test solution containing an adequate amount of nucleic acid can be prepared simply by treating a specimen with a bacteriolytic enzyme, a surfactant or an alkali for a short time.

Oligonucleotides used as primers in the present invention may be either synthetic or natural, and in view of selectivity, detection sensitivity and reproducibility, they are not less than 10 bases in length, preferably not less than 15 bases. It is not necessary to label the primers for detection.

The region to be amplified in a target gene (i.e., the Shiga toxin gene of Shigella species, the ipaH gene and the invE gene of EIEC, the VT1 gene and the VT2 gene of EHEC or V-TEC, the araC gene of Salmonella species, the TSST-1 gene of *Staphylococcus aureus*, and the ctx gene of *Vibrio cholerae*, and the enterotoxin gene of *Clostridium perfringens*) is 50 to 2000 bases in length, preferably 100 to 1000 bases.

In PCR, a thermostable DNA polymerase is used. The origins from which the enzyme is derived are not particularly limited as long as the enzyme maintains its activity at a temperature of from 90 to 95° C. The denaturation is carried out at a temperature of from 90 to 95° C., the primer annealing from 37 to 65° C., and the polymerization reaction from 50 to 75° C. The cycle of denaturation, primer annealing and polymerization is repeated for 20 to 42 cycles.

The presence or absence, and the length of the amplified nucleotide fragment can be detected by subjecting the reaction solution to agarose gel electrophoresis after the completion of PCR. Other types of electrophoresis and chromatography can also be used for the detection. One of the oligonucleotide primers may be used as a probe to detect the amplified nucleotide sequence.

The detection of a nucleotide sequence of a target gene in a specimen means that the bacterial strain having the gene is present in the specimen.

The invention will now be described in more detail by the following examples, but it should be noted that the invention is not limited to these examples.

EXAMPLES

Example 1

Detection of Shigella Species Having the Shigella Toxin Gene

[Experiment 1]

Preparation of Specimens

The 42 strains of *Shigella dysenteriae* listed in Table 1 are obtained from patients or other sources. Each strain is inoculated to LB medium (1% tryptone, 0.5% yeast extract, 1% sodium chloride), and subjected to overnight shaking culture at 37° C. under aerobic conditions. Each culture broth is diluted 10 folds with 10 mM Tris-HCl buffer, pH 7.5 (hereinafter referred to as TE buffer), and heated at 95° C. for 10 minutes, followed by centrifugation; the supernatants are used as specimen solutions.

Synthesis of Primers

As primers for amplifying the Shiga toxin gene of *Shigella dysenteriae*, the above-described oligonucleotides SEQ ID NO:1 and SEQ ID NO:2 are selected based upon the known base sequence of the Shiga toxin gene [Takao, T. et al., Microb. Pathog., 5:357–369 (1988)], and chemically synthesized by the β-cyanoethylphosphoamidite method using a Cyclone Plus DNA synthesizer (produced by MilliGen/Bioresearch). The synthesized oligonucleotides are purified by high performance liquid chromatography using a C18 reversed-phase column.

The Shiga toxin gene is regarded as identical to the VT1 gene of EHEC or VTEC, with difference only in several bases [Takao, T. et al., Microb. Pathog., 5:357–369 (1988)].

PCR

To 3 $\mu$l of the above-described specimen solution, 17.05 $\mu$l of sterile distilled water, 3 $\mu$l of 10×reaction buffer, 4.8 $\mu$l of dNTP solution, 1.0 $\mu$l of primer (1), 1.0 $\mu$l of primer (2), and 0.15 $\mu$l of a thermostable DNA polymerase are added to prepare 30 $\mu$l of a reaction mixture. This reaction mixture is overlaid with 50 $\mu$l of mineral oil (produced by SIGMA). The contents of the solutions used and the primers (1) and (2) are as follows:

10×reaction buffer: 500 mM KCl, 100 mM Tris-HC1, pH 8.3, 15 mM $MgCl_2$, 0.1% (w/v) gelatin.

dNTP solution: A mixture of dATP, dCTP, dGTP and dTTP, each having a final concentration of 1.25 mM.

Primers (1) and (2): Aqueous solution of the above-described chemically synthesized purified products (concentration, 3.75 OD/ml).

Primers: The above-described chemically synthesized and purified products are used in combination as follows:

Primer (1)+primer (2)=

Oligonucleotide SEQ ID NO:1+Oligonucleotide SEQ ID NO:2

Thermostable DNA polymerase: Taq DNA polymerase (5 unit/ml; produced by Perkin Elmer Cetus).

The reaction conditions are as follows:

Thermal denaturation: 94° C. for 1 minute.

Annealing: 55° C. for 1 minute.

Polymerization: 72° C. for 1 minute.

The cycle of thermal denaturation, primer annealing and polymerization (5.7 minutes) is repeated for 35 cycles (entire time, about 3 hours). This procedure is performed using a DNA thermal cycler (produced by Perkin Elmer Cetus) in which the above reaction conditions are programmed.

Detection

Agarose Gel Electrophoresis

To detect the amplified nucleotide fragment in the reaction mixture, agarose gel electrophoresis is conducted as mentioned below.

The agarose gel used has a gel concentration of 3% (w/v) and contains ethidium bromide (0.5 $\mu$l/ml). Electrophoresis is performed at the constant voltage of 100 V for 30 minutes. Operation procedures and other conditions described by Maniatis et al.[Molecular Cloning, 2nd edition (1989)] are used. In addition to the reaction mixture, molecular weight markers are also electrophoresed concurrently. The length of the nucleotide fragment is calculated by comparing the relative mobilities.

Reversed Passive Latex Agglutination (RPLA) Test

A commercially available RPLA kit for detection of *Escherichia coli* Verocytotoxin (produced by DENKA SEIKEN) is purchased. Specimens are prepared and tested according to the instruction manual attached.

Results

The base sequence of the Shiga toxin gene of *Shigella dysenteriae* has already been determined. Therefore, the length of the nucleotide amplified by PCR using the oligonucleotides of the present invention as primers can easily be estimated. Specifically, when the oligonucleotides SEQ ID NO: 1 and SEQ ID NO: 2 of the present invention are used in combination, a nucleotide sequence of 349 bases (or a nucleotide duplex of 349 base pairs) is amplified. When this estimation accords with the length of the amplified nucleotide fragment, it is judged that PCR using the combination of primers accurately amplify the target region of the Shiga toxin gene, and that the bacterial strain in the specimen has the Shiga toxin gene. The results obtained from the agarose gel electrophoresis with 34 test strains are given in Table 1. PCR using the primers of the present invention amplifies only the DNA of the strains which give positive results in the RPLA, showing no amplification of DNAs of Shiga toxin negative strains. This indicates that PCR using the primers of the present invention are capable of accurately amplifying the Shiga toxin gene and that *Shigella dysenteriae* having the Shiga toxin gene can be detected with high accuracy by using the oligonucleotides of the present invention.

TABLE 1

| No | Strains | | RPLA | PCR |
|---|---|---|---|---|
| 01 | S. dysenteriae | TUMD1 | − | − |
| 02 | S. dysenteriae | TUMD2 | − | − |
| 03 | S. dysenteriae | TUMD3 | − | − |
| 04 | S. dysenteriae | TUMD4 | − | − |
| 05 | S. dysenteriae | TUMD5 | − | − |
| 06 | S. dysenteriae | TUMD6 | − | − |
| 07 | S. dysenteriae | MARABLA | − | − |
| 08 | S. dysenteriae | AQ7003 | + | + |
| 09 | S. dysenteriae | AQ7004 | + | + |
| 10 | S. dysenteriae | AQ7018 | − | − |
| 11 | S. dysenteriae | AQ7029 | − | − |
| 12 | S. dysenteriae | AQ7030 | − | − |
| 13 | S. dysenteriae | AQ7061 | − | − |
| 14 | S. dysenteriae | AQ7125 | − | − |
| 15 | S. dysenteriae | AQ7131 | − | − |
| 16 | S. dysenteriae | AQ7151 | − | − |
| 17 | S. dysenteriae | AQ7164 | − | − |
| 18 | S. dysenteriae | AQ7166 | − | − |
| 19 | S. dysenteriae | AQ7234 | − | − |
| 20 | S. dysenteriae | AQ7302 | − | − |
| 21 | S. dysenteriae | AQ7350 | − | − |
| 22 | S. dysenteriae | AQ7370 | − | − |
| 23 | S. dysenteriae | AQ7403 | − | − |
| 24 | S. dysenteriae | AA-22021 | + | + |
| 25 | S. dysenteriae | AA-22184 | + | + |
| 26 | S. dysenteriae | AA-22192 | + | + |
| 27 | S. dysenteriae | AA-22555 | + | + |
| 28 | S. dysenteriae | AA-21933 | + | + |
| 29 | S. dysenteriae | AA-22496 | + | + |
| 30 | S. dysenteriae | AA-22224 | + | + |
| 31 | S. dysenteriae | AA-22542 | + | + |
| 32 | S. dysenteriae | AA-22616 | + | + |
| 33 | S. dysenteriae | AA-22239 | + | + |
| 34 | S. dysenteriae | AA-22538 | + | + |
| 35 | S. dysenteriae | ATCC9361 | + | + |
| 36 | S. dysenteriae | ATCC9753 | − | − |
| 37 | S. dysenteriae | ATCC9764 | − | − |
| 38 | S. dysenteriae | ATCC11456a | + | + |
| 39 | S. dysenteriae | ATCC13313 | + | + |
| 40 | S. dysenteriae | ATCC23351 | + | + |

TABLE 1-continued

| No | Strains | | RPLA | PCR |
|---|---|---|---|---|
| 41 | S. dysenteriae | ATCC29027 | − | − |
| 42 | S. dysenteriae | ATCC29028 | − | − |

Note)
+: DNA of estimated length is amplified.
N: DNA of not-estimated length is amplified.
−: DNA is not amplified.

[Experiment 2]

To determine whether the results obtained in Experiment 1 are specific to the Shiga toxin gene, the DNAs of clinically important pathogenic bacteria other than Shigella dysenteriae are examined with the primers of the present invention. The same procedure as used in Experiment 1 is followed, except for the method of preparation of specimens.

Preparation of Specimens

Each strain listed in Table 2 is inoculated to an appropriate enrichment medium, and subjected to overnight culture at 37° C. under aerobic or anaerobic conditions (*Clostridium perfringens, Campylobacter jejune, Campylobacter coli, Bacteroides flagilis, Bacteroides vulgatus, Lactobacillus acidophilus,* and *Bifidobacterium adolescentis* are cultured under anaerobic conditions, while *Neisseria gonorrhoeae* and *Neisseria meningitidis* are cultured in the presence of 3–10% $CO_2$). Bacterial cells are centrifugally recovered from 0.5 ml of each culture broth, and once washed with TE buffer. To these bacterial cells, an N-acetylmuraminidase solution in 50 mM phosphate buffer, pH 7.5, and an achromopeptidase solution in the same buffer are added to final concentrations of 50 $\mu$g/ml and 1 mg/ml, respectively, followed by incubation at 37° C. for 10 minutes to lyse the cells. A 1:1 phenol/chloroform mixture, saturated with TE buffer, is added to the lysate, followed by vigorous stirring. After centrifugation, the supernatant is recovered, and treated with ethanol to precipitate the nucleic acids. The resulting precipitate is dissolved in 1 ml of TE buffer; this solution is used as a specimen. Also, Human placenta DNA, at a concentration of 1 $\mu$g/ml, is subjected to PCR in the same manner as above.

Results

Table 2 shows the results of the test using the combination of the primers of the present invention. This combination of primers does not amplify DNAs other than those of Shiga toxin-producing *Shigella dysenteriae* and Verocytotoxin-1-producing *Escherichia coli*. It can therefore be concluded that the oligonucleotide primers of the present invention selectively react with DNAs of the bacteria having the Shiga toxin gene.

The agarose gel electrophoresis used in the above examples of the present invention can differentiate nucleotide fragments from one another which are different in length by 5–10 bases (base pairs) for nucleotide fragments of not more than 100 bases (base pairs), and by 10–20 bases (base pairs) for nucleotide fragments of 100–500 bases (base pairs). In addition, the use of other gel material such as acrylamide makes it possible to improve the precision in measuring the length of nucleotide fragment. Thus,. the reliability of the selective detection of the target gene in the present invention can further be increased.

TABLE 2

| No | Strains | | PCR |
|---|---|---|---|
| 01 | *Bacillus cereus* | ATCC14579 | − |
| 02 | *Bacillus Subtilis* | JCM1465 | − |
| 03 | *Staphylococcus aureus* | JCM2413 | − |
| 04 | *Staphylococcus epidermidis* | JCM2414 | − |
| 05 | *Salmonella typhimurium* | IFO12529 | − |
| 06 | *Salmonella enteritidis* | IFO3163 | − |
| 07 | *Clostridium perfringens* | ATCC12917 | − |
| 08 | *Vibrio cholerae* | ATCC25872 | − |
| 09 | *Vibrio cholerae* type Ogawa | ATCC9458 | − |
| 10 | *Vibrio cholerae* type Inaba | ATCC9459 | − |
| 11 | *Vibrio fluvialis* | JCM3752 | − |
| 12 | *Campylobacter jejuni* | JCM2013 | − |
| 13 | *Campylobacter coli* | JCM2529 | − |
| 14 | *Escherichia coli* | JCM1649 | − |
| 15 | *Yersinia enterocolitica* | ATCC9610 | − |
| 16 | *Shigella flexneri* | ATCC29903 | − |
| 17 | *Shigella sonnei* | ATCC29930 | − |
| 18 | *Bacteroides flagilis* | ATCC23745 | − |
| 19 | *Bacteroides vulgatus* | JCM5826 | − |
| 20 | *Enterococcus faecalis* | JCM5803 | − |
| 21 | *Klebsiella pneumoniae* | JCM1662 | − |
| 22 | *Proteus vulgaris* | JCM1668 | − |
| 23 | *Citrobacter freundii* | ATCC33128 | − |
| 24 | *Streptococcus pyogenes* | ATCC12344 | − |
| 25 | *Streptococcus pneumoniae* | ATCC33400 | − |
| 26 | *Elaemophilus influenzae* | ATCC33391 | − |
| 27 | *Proteus mirabilis* | ATCC29906 | − |
| 28 | *Neisseria meningitidis* | ATCC13077 | − |
| 29 | *Neisseria gonorrhoeae* | ATCC19424 | − |
| 30 | *Listeria monocytogenes* | ATCC15313 | − |
| 31 | *Lactobacillus acidophilus* | JCM1132 | − |
| 32 | *Bifidobacterium adolescentis* | JCM1275 | − |
| 33 | *Fusobacterium nucleatum* | ATCC25586 | − |
| 34 | *Propionibacterium acnes* | ATCC6919 | − |
| 35 | *Veillonella atypica* | ATCC17744 | − |
| 36 | *Pseudomonas aeruginosa* | IFO12689 | − |
| 37 | *Corynebacterium diphtheriae* | JCM1310 | − |
| 38 | *Peptostreptococcus anaerobius* | ATCC27337 | − |
| 39 | Human placental DNA | | − |

Note)
+: DNA of estimated length is amplified.
N: DNA of not-estimated length is amplified.
−: DNA is not amplified.

Example 2

Detection of Shigella Species and EIEC both Having the ipaH Gene

[Experiment 1]

Preparation of Specimens

The same procedure as used in Example 1 is followed except that 341 strains of Shigella species and EIEC listed in Tables 3-1 to 3-7 are used.

Synthesis of Primers

As primers for amplifying the ipah gene of Shigella species and EIEC strains, the above-described oligonucleotides SEQ ID NO:3 and SEQ ID NO:4 are selected based upon the known base sequence of the ipaH gene [Hartman, A. B., et al., J. Bacteriol., 172, 1905–1915(1990); Venkatesan, M. M., et al., Mol. Microbiol., 5, 2435–2446 (1991)]. These oligonucleotides are chemically synthesized by the same method as in Experiment 1 of Example 1.

PCR

PCR is carried out under the same reaction conditions as in Example 1 except that the following oligonucleotide combination is used:

Primer (1)+primer (2)=Oligonucleotide SEQ ID NO:3+Oligonucleotide SEQ ID NO:4

Detection

Agarose Gel Electrophoresis

The same procedure as in Example 1 is followed.

Colony Hybridization Test

A colony hybridization test is carried out using an oligonucleotide probe specific to the ipaH gene according to the procedure described by Grunstein [Grunstein, M. and Hogness, D., Proc. Natl. Acad. Sci., 72, 3961(1975)].

Results

The base sequence of the ipaH gene of Shigella species and EIEC has already been determined. Therefore, the length of the nucleotide fragments amplified by PCR using the oligonucleotides of the present invention as primers can easily be estimated. Specifically, when the oligonucleotides SEQ ID NO: 3 and SEQ ID NO: 4 of the present invention are used in combination, a nucleotide fragment of 242 bases (or a nucleotide duplex of 242 base pairs) should be amplified. When this estimation accords with the length of the amplified nucleotide fragment, it is judged that PCR using the combination of primers accurately amplify the target region in the ipaH gene, and that the bacterial strain in the specimen has the ipaH gene. The results obtained from the agarose gel electrophoresis with 341 test strains are given in Tables 3-1 to 3-7. PCR using the primers of the present invention amplifies only the DNA of the strains which give the ipaH positive results in the colony hybridization test, showing no amplification of the DNAs of ipaH negative strains. This indicates that PCR using the primers of the present invention is capable of accurately amplifying the ipaH gene and that Shigella species and EIEC both having the ipaH gene can be detected with high accuracy by using the oligonucleotides of the present invention.

TABLE 3

| No | Strains | | CH test* | Primer 3 + 4** |
|---|---|---|---|---|
| 001 | *S. dysenteriae* | TUMD1 | + | + |
| 002 | *S. dysenteriae* | TUMD2 | + | + |
| 003 | *S. dysenteriae* | TUMD3 | + | + |
| 004 | *S. dysenteriae* | TUMD4 | + | + |
| 005 | *S. dysenteriae* | TUMD5 | + | + |
| 006 | *S. dysenteriae* | TUMD6 | + | + |
| 007 | *S. dysenteriae* | MARABIA | − | − |
| 008 | *S. dysenteriae* | AQ-7003 | + | + |
| 009 | *S. dysenteriae* | AQ-7004 | + | + |
| 010 | *S. dysenteriae* | AQ-7018 | + | + |
| 011 | *S. dysenteriae* | AQ-7029 | + | + |
| 012 | *S. dysenteriae* | AQ-7030 | + | + |
| 013 | *S. dysenteriae* | AQ-7061 | + | + |
| 014 | *S. dysenteriae* | AQ-7125 | + | + |
| 015 | *S. dysenteriae* | AQ-7131 | + | + |
| 016 | *S. dysenteriae* | AQ-7151 | + | + |
| 017 | *S. dysenteriae* | AQ-7164 | + | + |
| 018 | *S. dysenteriae* | AQ-7166 | + | + |
| 019 | *S. dysenteriae* | AQ-7234 | + | + |
| 020 | *S. dysenteriae* | AQ-7302 | + | + |
| 021 | *S. dysenteriae* | AQ-7350 | + | + |
| 022 | *S. dysenteriae* | AQ-7370 | + | + |
| 023 | *S. dysenteriae* | AQ-7403 | + | + |
| 024 | *S. dysenteriae* | AA-22021 | + | + |
| 025 | *S. dysenteriae* | AA-22184 | + | + |
| 026 | *S. dysenteriae* | AA-22192 | + | − |
| 027 | *S. dysenteriae* | AA-22555 | + | − |
| 028 | *S. dysenteriae* | AA-21933 | + | + |
| 029 | *S. dysenteriae* | AA-22496 | + | + |
| 030 | *S. dysenteriae* | AA-22224 | + | + |
| 031 | *S. dysenteriae* | AA-22542 | + | + |
| 032 | *S. dysenteriae* | AA-22616 | − | + |
| 033 | *S. dysenteriae* | AA-22239 | + | + |
| 034 | *S. dysenteriae* | AA-22538 | + | + |
| 035 | *S. dysenteriae* | ATCC9361 | + | + |
| 036 | *S. dysenteriae* | ATCC9753 | + | + |
| 037 | *S. dysenteriae* | ATCC11456a | + | + |
| 038 | *S. dysenteriae* | ATCC13313 | + | + |
| 039 | *S. dysenteriae* | ATCC23351 | + | + |

TABLE 3-continued

| No | Strains | | CH test* | Primer 3 + 4** |
|---|---|---|---|---|
| 040 | S. dysenteriae | ATCC29027 | + | + |
| 041 | S. dysenteriae | ATCC29028 | + | + |
| 042 | S. flexneri | TUMD7 | + | + |
| 043 | S. flexneri | TUMD8 | + | + |
| 044 | S. flexneri | TUMD9 | + | + |
| 045 | S. flexneri | TUMD10 | + | + |
| 046 | S. flexneri | TUMD11 | + | + |
| 047 | S. flexneri | TUMD12 | + | + |
| 048 | S. flexneri | TUMD13 | + | + |
| 049 | S. flexneri | TUMD14 | + | + |
| 050 | S. flexneri | TUMD15 | + | + |
| 051 | S. flexneri | TUMD16 | + | + |
| 052 | S. flexneri | TUMD17 | + | + |
| 053 | S. flexneri | TUMD18 | + | + |
| 054 | S. flexneri | TUMD19 | + | + |
| 055 | S. flexneri | TUMD20 | + | + |
| 056 | S. flexneri | TUMD21 | + | + |
| 057 | S. flexneri | TUMD22 | + | + |
| 058 | S. flexneri | TUMD23 | + | + |
| 059 | S. flexneri | TUMD24 | + | + |
| 060 | S. flexneri | TUMD25 | + | + |
| 061 | S. flexneri | TUMD26 | + | + |
| 062 | S. flexneri | TUMD27 | + | + |
| 063 | S. flexneri | TUMD28 | + | + |
| 064 | S. flexneri | TUMD29 | + | + |
| 065 | S. flexneri | TUMD30 | + | + |
| 066 | S. flexneri | TUMD31 | + | + |
| 067 | S. flexneri | TUMD32 | + | + |
| 068 | S. flexneri | TUMD33 | + | + |
| 069 | S. flexneri | TUMD34 | + | + |
| 070 | S. flexneri | TUMD35 | + | + |
| 071 | S. flexneri | TUMD36 | + | + |
| 072 | S. flexneri | TUMD38 | + | + |
| 073 | S. flexneri | TUMD39 | + | + |
| 074 | S. flexneri | TUMD40 | + | + |
| 075 | S. flexneri | TUMD41 | + | + |
| 076 | S. flexneri | TUMD42 | + | + |
| 077 | S. flexneri | TUMD43 | + | + |
| 078 | S. flexneri | TUMD44 | + | + |
| 079 | S. flexneri | TUMD45 | + | + |
| 080 | S. flexneri | TUMD46 | + | + |
| 081 | S. flexneri | TUMD47 | + | + |
| 082 | S. flexneri | TUMD48 | + | + |
| 083 | S. flexneri | TUMD49 | + | + |
| 084 | S. flexneri | TUMD50 | + | + |
| 085 | S. flexneri | TUMD51 | + | + |
| 086 | S. flexneri | TUMD52 | + | + |
| 087 | S. flexneri | TUMD53 | + | + |
| 088 | S. flexneri | TUMD54 | + | + |
| 089 | S. flexneri | TUMD55 | + | + |
| 090 | S. flexneri | TUMD56 | + | + |
| 091 | S. flexneri | TUMD57 | + | + |
| 092 | S. flexneri | TUMD58 | + | + |
| 093 | S. flexneri | TUMD59 | + | + |
| 094 | S. flexneri | TUMD60 | + | + |
| 095 | S. flexneri | TUMD61 | + | + |
| 096 | S. flexneri | Maramba 89-77 | + | + |
| 097 | S. flexneri | Maramba 89-95 | + | + |
| 098 | S. flexneri | Maramba 89-109a | + | + |
| 099 | S. flexneri | Maramba 89-119 | + | + |
| 100 | S. flexneri | Maramba 89-155 | + | + |
| 101 | S. flexneri | Maramba 89-164 | + | + |
| 102 | S. flexneri | Maramba 89-150 | + | + |
| 103 | S. flexneri | AA-22175 | + | + |
| 104 | S. flexneri | AA-22371 | + | + |
| 105 | S. flexneri | AA-22266 | + | + |
| 106 | S. flexneri | AA-22636 | + | + |
| 107 | S. flexneri | AA-22187 | + | + |
| 108 | S. flexneri | AA-22170 | + | + |
| 109 | S. flexneri | AA-22367 | + | + |
| 110 | S. flexneri | AA-22316 | + | + |
| 111 | S. flexneri | AA-22265 | + | + |
| 112 | S. flexneri | AA-22296 | + | + |
| 113 | S. flexneri | AA-22312 | + | + |
| 114 | S. flexneri | AA-22246 | + | + |
| 115 | S. flexneri | AA-21981 | + | + |
| 116 | S. flexneri | AA-22097 | + | + |
| 117 | S. flexneri | AQ-7347 | + | + |
| 118 | S. flexneri | AQ-7348 | + | + |
| 119 | S. flexneri | AQ-7351 | + | + |
| 120 | S. flexneri | AQ-7360 | + | + |
| 121 | S. flexneri | AQ-7367 | + | + |
| 122 | S. flexneri | AQ-7372 | + | + |
| 123 | S. flexneri | AQ-7378 | + | + |
| 124 | S. flexneri | AQ-7379 | + | + |
| 125 | S. flexneri | AQ-7380 | + | + |
| 126 | S. flexneri | AQ-7385 | + | + |
| 127 | S. flexneri | AQ-7386 | + | + |
| 128 | S. flexneri | AQ-7390 | + | + |
| 129 | S. flexneri | AQ-7391 | + | + |
| 130 | S. flexneri | AQ-7393 | + | + |
| 131 | S. flexneri | AQ-7394 | + | + |
| 132 | S. flexneri | AQ-7398 | + | + |
| 133 | S. flexneri | AQ-7399 | + | + |
| 134 | S. flexneri | AQ-7400 | + | + |
| 135 | S. flexneri | AQ-7402 | + | + |
| 136 | S. flexneri | AQ-7407 | + | + |
| 137 | S. flexneri | AQ-7408 | + | + |
| 138 | S. flexneri | AQ-7411 | + | + |
| 139 | S. flexneri | AQ-7416 | + | + |
| 140 | S. flexneri | AQ-7417 | + | + |
| 141 | S. flexneri | AQ-7418 | + | + |
| 142 | S. flexneri | AQ-7423 | + | + |
| 143 | S. flexneri | AQ-7424 | + | + |
| 144 | S. flexneri | AQ-7426 | + | + |
| 145 | S. flexneri | AQ-7427 | + | + |
| 146 | S. flexneri | Manila 89-164 | + | − |
| 147 | S. flexneri | Manila 89-177 | + | + |
| 148 | S. flexneri | Manila 89-209 | + | + |
| 149 | S. flexneri | Manila 89-210 | + | + |
| 150 | S. flexneri | Manila 89-229 | + | + |
| 151 | S. flexneri | Manila 89-230 | − | − |
| 152 | S. flexneri | Manila 89-231 | + | + |
| 153 | S. flexneri | Manila 89-232 | + | + |
| 154 | S. flexneri | Manila 89-233 | + | + |
| 155 | S. flexneri | Manila 89-273 | + | + |
| 156 | S. flexneri | Manila 89-328 | + | + |
| 157 | S. flexneri | Manila 89-333 | + | + |
| 158 | S. flexneri | Manila 89-365 | + | + |
| 159 | S. flexneri | Manila 89-274 | + | + |
| 160 | S. flexneri | Manila 89-436 | + | + |
| 161 | S. flexneri | Manila 89-438 | + | + |
| 162 | S. flexneri | Manila 89-443 | + | + |
| 163 | S. flexneri | Manila 89-444 | + | + |
| 164 | S. flexneri | Manila 89-450 | + | + |
| 165 | S. flexneri | Manila 89-480 | + | + |
| 166 | S. flexneri | Manila 89-483 | + | + |
| 167 | S. flexneri | Manila 89-486 | + | + |
| 168 | S. flexneri | Manila 89-498 | + | + |
| 169 | S. flexneri | Manila 89-499 | − | − |
| 170 | S. flexneri | Manila 89-503 | + | + |
| 171 | S. flexneri | Manila 89-509 | + | + |
| 172 | S. flexneri | Manila 89-532 | + | + |
| 173 | S. flexneri | Manila 89-539 | − | − |
| 174 | S. boydii | TUMD62 | + | + |
| 175 | S. boydii | TUMD63 | + | + |
| 176 | S. boydii | TUMD64 | + | + |
| 177 | S. boydii | TUMD65 | + | + |
| 178 | S. boydii | TUMD66 | + | + |
| 179 | S. boydii | TUMD67 | + | + |
| 180 | S. boydii | TUMD68 | + | + |
| 181 | S. boydii | AQ-7019 | + | + |
| 182 | S. boydii | AQ-7020 | + | + |
| 183 | S. boydii | AQ-7026 | + | + |
| 184 | S. boydii | AQ-7032 | + | + |
| 185 | S. boydii | AQ-7039 | + | + |
| 186 | S. boydii | AQ-7042 | + | + |
| 187 | S. boydii | AQ-7062 | + | + |
| 188 | S. boydii | AQ-7076 | + | + |
| 189 | S. boydii | AQ-7098 | + | + |
| 190 | S. boydii | AQ-7157 | + | + |
| 191 | S. boydii | AQ-7193 | + | + |

TABLE 3-continued

| No | Strains | | CH test* | Primer 3 + 4** |
|---|---|---|---|---|
| 192 | S. boydii | AQ-7206 | + | + |
| 193 | S. boydii | AQ-7213 | + | + |
| 194 | S. boydii | AQ-7218 | + | + |
| 195 | S. boydii | AQ-7238 | + | + |
| 196 | S. boydii | AQ-7267 | + | + |
| 197 | S. boydii | AQ-7268 | + | + |
| 198 | S. boydii | AQ-7307 | + | + |
| 199 | S. boydii | AQ-7313 | + | + |
| 200 | S. boydii | AQ-7314 | + | + |
| 201 | S. boydii | AQ-7324 | − | − |
| 202 | S. boydii | AQ-7349 | + | + |
| 203 | S. boydii | AQ-7354 | + | + |
| 204 | S. boydii | AQ-7356 | + | + |
| 205 | S. boydii | AQ-7357 | + | + |
| 206 | S. boydii | AQ-7368 | + | + |
| 207 | S. boydii | AQ-7373 | + | + |
| 208 | S. boydii | AQ-7376 | + | + |
| 209 | S. boydii | AQ-7405 | + | + |
| 210 | S. boydii | AA-22562 | + | + |
| 211 | S. boydii | AA-22241 | − | − |
| 212 | S. boydii | AA-22610 | − | − |
| 213 | S. boydii | AA-20255 | + | + |
| 214 | S. boydii | AA-20211 | + | + |
| 215 | S. boydii | AA-21713 | + | + |
| 216 | S. boydii | AA-17405 | − | − |
| 217 | S. boydii | AA-22804 | + | + |
| 218 | S. boydii | AQ-7297 | + | + |
| 219 | S. sonnei | AQ-7366 | + | + |
| 220 | S. sonnei | AQ-7369 | + | + |
| 221 | S. sonnei | AQ-7371 | + | + |
| 222 | S. sonnei | AQ-7374 | + | + |
| 223 | S. sonnei | AQ-7375 | + | + |
| 224 | S. sonnei | AQ-7377 | + | + |
| 225 | S. sonnei | AQ-7381 | + | + |
| 226 | S. sonnei | AQ-7382 | + | + |
| 227 | S. sonnei | AQ-7383 | + | + |
| 228 | S. sonnei | AQ-7384 | + | + |
| 229 | S. sonnei | AQ-7387 | + | + |
| 230 | S. sonnei | AQ-7388 | + | + |
| 231 | S. sonnei | AQ-7389 | + | + |
| 232 | S. sonnei | AQ-7392 | + | + |
| 233 | S. sonnei | AQ-7395 | + | + |
| 234 | S. sonnei | AQ-7396 | + | + |
| 235 | S. sonnei | AQ-7397 | + | + |
| 236 | S. sonnei | AQ-7401 | + | + |
| 237 | S. sonnei | AQ-7406 | + | + |
| 238 | S. sonnei | AQ-7409 | + | + |
| 239 | S. sonnei | AQ-7410 | + | + |
| 240 | S. sonnei | AQ-7412 | + | + |
| 241 | S. sonnei | AQ-7413 | + | + |
| 242 | S. sonnei | AQ-7414 | + | + |
| 243 | S. sonnei | AQ-7415 | + | + |
| 244 | S. sonnei | AQ-7419 | + | + |
| 245 | S. sonnei | AQ-7420 | + | + |
| 246 | S. sonnei | AQ-7421 | + | + |
| 247 | S. sonnei | AQ-7422 | + | + |
| 248 | S. sonnei | AQ-7425 | + | + |
| 249 | S. sonnei | AA-22634 | + | + |
| 250 | S. sonnei | AA-22677 | + | + |
| 251 | S. sonnei | AA-18306 | + | + |
| 252 | S. sonnei | AA-22067 | + | + |
| 253 | S. sonnei | AA-22870 | + | + |
| 254 | S. sonnei | TUMD69 | + | + |
| 255 | S. sonnei | TUMD70 | + | + |
| 256 | S. sonnei | TUMD71 | + | + |
| 257 | S. sonnei | TUMD72 | + | + |
| 258 | S. sonnei | TUMD73 | + | + |
| 259 | S. sonnei | TUMD74 | + | + |
| 260 | S. sonnei | TUMD75 | + | + |
| 261 | S. sonnei | TUMD76 | + | + |
| 262 | S. sonnei | TUMD77 | + | + |
| 263 | S. sonnei | TUMD78 | + | + |
| 264 | S. sonnei | TUMD79 | + | + |
| 265 | S. sonnei | TUMD80 | + | + |
| 266 | S. sonnei | TUMD81 | + | + |
| 267 | S. sonnei | TUMD82 | + | + |
| 268 | S. sonnei | TUMD83 | + | + |
| 269 | S. sonnei | TUMD84 | + | + |
| 270 | S. sonnei | TUMD85 | + | + |
| 271 | S. sonnei | TUMD86 | + | + |
| 272 | S. sonnei | TUMD87 | + | + |
| 273 | S. sonnei | TUMD88 | + | + |
| 274 | S. sonnei | TUMD89 | + | + |
| 275 | S. sonnei | TUMD90 | + | + |
| 276 | S. sonnei | TUMD91 | + | + |
| 277 | S. sonnei | TUMD92 | + | − |
| 278 | S. sonnei | TUMD93 | + | + |
| 279 | S. sonnei | TUMD94 | + | + |
| 280 | S. sonnei | TUMD95 | + | + |
| 281 | S. sonnei | TUMD96 | + | + |
| 282 | S. sonnei | TUMD97 | + | + |
| 283 | S. sonnei | TUMD98 | + | + |
| 284 | S. sonnei | TUMD99 | + | + |
| 285 | S. sonnei | TUMD100 | + | + |
| 286 | S. sonnei | TUMD101 | + | + |
| 287 | S. sonnei | TUMD102 | + | + |
| 288 | S. sonnei | TUMD103 | + | + |
| 289 | S. sonnei | TUMD104 | + | + |
| 290 | S. sonnei | TUMD105 | + | + |
| 291 | S. sonnei | TUMD106 | + | + |
| 292 | S. sonnei | TUMD107 | + | + |
| 293 | S. sonnei | TUMD108 | + | + |
| 294 | S. sonnei | TUMD109 | + | + |
| 295 | S. sonnei | TUMD110 | + | + |
| 296 | S. sonnei | TUMD111 | + | + |
| 297 | S. sonnei | TUMD112 | + | + |
| 298 | S. sonnei | TUMD113 | + | + |
| 299 | S. sonnei | TUMD114 | + | + |
| 200 | S. sonnei | TUMD115 | + | + |
| 301 | S. sonnei | TUMD116 | + | + |
| 302 | S. sonnei | TUMD117 | + | + |
| 303 | S. sonnei | TUMD118 | + | + |
| 304 | S. sonnei | TUMD119 | + | + |
| 305 | S. sonnei | TUMD120 | + | + |
| 306 | S. sonnei | TUMD121 | + | + |
| 307 | S. sonnei | TUMD122 | + | + |
| 308 | S. sonnei | TUMD123 | + | + |
| 309 | S. sonnei | TUMD124 | + | + |
| 310 | S. sonnei | TUMD125 | + | + |
| 311 | S. sonnei | TUMD126 | + | + |
| 312 | S. sonnei | TUMD127 | + | + |
| 313 | S. sonnei | TUMD128 | + | + |
| 314 | S. sonnei | Maramba 89-154 | + | + |
| 315 | S. sonnei | Maramba 89-161 | + | + |
| 316 | S. sonnei | Manila 89-342 | + | + |
| 317 | S. sonnei | Manila 89-445 | + | + |
| 318 | E. coli | DMR6 | + | + |
| 319 | E. coli | DMR78 | + | + |
| 320 | E. coli | DMR79 | + | + |
| 321 | E. coli | AQ8001 | + | + |
| 322 | E. coli | AQ8003 | + | + |
| 323 | E. coli | AQ8004 | + | + |
| 324 | E. coli | AQ8008 | + | + |
| 325 | E. coli | AQ8010 | + | + |
| 326 | E. coli | AQ8011 | + | + |
| 327 | E. coli | AQ8012 | + | + |
| 328 | E. coli | AQ8013 | + | + |
| 329 | E. coli | AQ8016 | + | + |
| 330 | E. coli | AQ8019 | + | + |
| 331 | E. coli | AQ8022 | + | + |
| 332 | E. coli | AQ8024 | + | + |
| 333 | E. coli | AQ8025 | + | + |
| 334 | E. coli | AQ8027 | + | + |
| 335 | E. coli | AQ8028 | + | + |
| 336 | E. coli | AQ8029 | + | + |
| 337 | E. coli | AQ8031 | + | + |
| 338 | E. coli | AQ8033 | − | − |
| 339 | E. coli | AQ8036 | − | − |

TABLE 3-continued

| No | Strains | | CH test* | Primer 3 + 4** |
|---|---|---|---|---|
| 340 | E. coli | AQ8044 | + | + |
| 341 | E. coli | PE660 | + | + |

Note)
*Colony hybridization test
**Numerals refer to SEQ ID NOs.

[Experiment 2]

To determine whether the results obtained in Experiment 1 are specific to the ipaH gene, the DNAs of clinically important pathogenic bacteria other than Shigella species and EIEC are examined with the primers of the present invention. The same procedure as used in Experiment 1 is followed, except for the procedure of preparation of specimens.

Preparation of Specimens

Each strain listed in Table 4 is treated in the same manner as in Experiment 2 of Example 1.

Results

Table 4 shows the results of the test using the combination of primers of the present invention. This combination of primers does not amplify any DNAs other than those of Shigella species and EIEC. It can therefore be concluded that the oligonucleotide primers of the present invention selectively react with DNAs of the bacteria having the ipah gene.

TABLE 4

| No | Strains | | PCR |
|---|---|---|---|
| 01 | Bacillus cereus | ATCC14579 | − |
| 02 | Bacillus Subtilis | JCM1465 | − |
| 03 | Staphylococcus aureus | JCM2413 | − |
| 04 | Staphylococcus epidermidis | JCM2414 | − |
| 05 | Salmonella typhimurium | IFO12529 | − |
| 06 | Salmonella enteritidis | IFO3163 | − |
| 07 | Clostridium perfringens | ATCC12917 | − |
| 08 | Vibrio cholerae | ATCC25872 | − |
| 09 | Vibrio cholerae type Ogawa | ATCC9458 | − |
| 10 | Vibrio cholerae type Inaba | ATCC9459 | − |
| 11 | Vibrio fluvialis | JCM3752 | − |
| 12 | Campylobacter jejuni | JCM2013 | − |
| 13 | Campylobacter coli | JCM2529 | − |
| 14 | Escherichia coli | JCM1649 | − |
| 15 | Yersinia enterocolitica | ATCC9610 | − |
| 16 | Corynebacterium diphtheriae | JCM13 | − |
| 17 | Peptostreptococcus anaerobius | ATCC23745 | − |
| 18 | Bacteroides flagilis | ATCC23745 | − |
| 19 | Bacteroides vulgatus | JCM5826 | − |
| 20 | Enterococcus faecalis | JCM5803 | − |
| 21 | Klebsiella pneumoniae | JCM1662 | − |
| 22 | Proteus vulgaris | JCM1668 | − |
| 23 | Citrobacter freundii | ATCC33128 | − |
| 24 | Streptococcus pyogenes | ATCC12344 | − |
| 25 | Streptococcus pneumoniae | ATCC33400 | − |
| 26 | Elaemophilis influenzae | ATCC33391 | − |
| 27 | Proteus mirabilis | ATCC29906 | − |
| 28 | Neisseria meningitidis | ATCC13077 | − |
| 29 | Neisseria gonorrhoeae | ATCC19424 | − |
| 30 | Listeria monocytogenes | ATCC15313 | − |
| 31 | Lactobacillus acidophilus | JCM1132 | − |
| 32 | Bifidobacterium adolescentis | JCM1275 | − |
| 33 | Fusobacterium nucleatum | ATCC25586 | − |
| 34 | Propionibacterium acnes | ATCC6919 | − |
| 35 | Veillonella atypica | ATCC17744 | − |
| 36 | Pseudomonas aeruginosa | IFO12689 | − |
| 37 | Human placental DNA | | − |

Example 3

Detection of Shigella Species and EIEC Having the invE Gene

[Experiment 1]

Preparation of Specimens

The same procedure as used in Example 1 is followed except that 341 strains of Shigella species and EIEC listed in Tables 3-1 to 3-7 are used.

Synthesis of Primers

As primers for amplifying the invE gene of Shigella species and EIEC, the above-described oligonucleotides SEQ ID NO:5 and SEQ ID NO:6 are selected based upon the known base sequence of the invE gene [Watanabe, H., et al., J. Bacteriol., 172, 619–629(1990)]. These oligonucleotides are chemically synthesized by the same method as in Experiment 1 of Example 1.

PCR

PCR is carried out under the same reaction conditions as in Example 1 except that the following oligonucleotide combination is used:

Primer (1)+primer (2)=
Oligonucleotide SEQ ID NO:5+Oligonucleotide SEQ ID NO:6

Detection

Agarose Gel Electrophoresis

The same procedure as in Example 1 is followed.

Colony Hybridization Test

A colony hybridization test is carried out using an oligonucleotide probe specific to invE gene according to the procedure described by Grunstein [Grunstein, M. and Hogness, D., Proc. Natl. Acad. Sci., 72, 3961(1975)].

Results

The base sequence of the invE gene of Shigella species and EIEC has already been determined. Therefore, the length of the nucleotide fragments amplified by PCR using the oligonucleotides of the present invention as primers can easily be estimated. Specifically, the oligonucleotides SEQ ID NO: 5 and SEQ ID NO: 6 of the present invention are used in combination, a nucleotide fragment of 293 bases (or a nucleotide duplex of 293 base pairs) should be amplified. When this estimation accords with the length of the amplified nucleotide sequence, it is judged that the combination of primers accurately amplifies the target region in the invE gene, and that the bacterial strain in the specimen has the invE gene. The results obtained from the agarose gel electrophoresis with 341 test strains are given in Tables 5-1 to 5-7. PCR using the primers of the present invention amplifies only the DNA of the strains which give the invE positive results in the colony hybridization test, showing no amplification of DNAs of invE negative strains. This indicates that PCR using the primers of the present invention is capable of accurately amplifying the invE gene and that Shigella species and EIEC both having the invE gene can be detected with high accuracy by using the oligonucleotides of the present invention.

TABLE 5

| No | Strains | | CH test* | Primer 5 + 6** |
|---|---|---|---|---|
| 001 | S. dysenteriae | TUMD1 | − | − |
| 002 | S. dysenteriae | TUMD2 | − | − |
| 003 | S. dysenteriae | TUMD3 | − | − |
| 004 | S. dysenteriae | TUMD4 | + | + |
| 005 | S. dysenteriae | TUMD5 | − | − |
| 006 | S. dysenteriae | TUMD6 | − | − |

TABLE 5-continued

| No | Strains | | CH test* | Primer 5 + 6** |
|---|---|---|---|---|
| 007 | S. dysenteriae | MARABIA | − | − |
| 008 | S. dysenteriae | AQ-7003 | − | − |
| 009 | S. dysenteriae | AQ-7004 | + | + |
| 010 | S. dysenteriae | AQ-7018 | − | − |
| 011 | S. dysenteriae | AQ-7029 | − | − |
| 012 | S. dysenteriae | AQ-7030 | + | + |
| 013 | S. dysenteriae | AQ-7061 | − | − |
| 014 | S. dysenteriae | AQ-7125 | + | + |
| 015 | S. dysenteriae | AQ-7131 | − | − |
| 016 | S. dysenteriae | AQ-7151 | − | − |
| 017 | S. dysenteriae | AQ-7164 | + | + |
| 018 | S. dysenteriae | AQ-7166 | + | + |
| 019 | S. dysenteriae | AQ-7234 | + | + |
| 020 | S. dysenteriae | AQ-7302 | − | − |
| 021 | S. dysenteriae | AQ-7350 | + | + |
| 022 | S. dysenteriae | AQ-7370 | + | + |
| 023 | S. dysenteriae | AQ-7403 | + | + |
| 024 | S. dysenteriae | AA-22021 | + | + |
| 025 | S. dysenteriae | AA-22184 | − | − |
| 026 | S. dysenteriae | AA-22192 | − | − |
| 027 | S. dysenteriae | AA-22555 | + | + |
| 028 | S. dysenteriae | AA-21933 | + | + |
| 029 | S. dysenteriae | AA-22496 | + | + |
| 030 | S. dysenteriae | AA-22224 | − | − |
| 031 | S. dysenteriae | AA-22542 | + | + |
| 032 | S. dysenteriae | AA-22616 | − | − |
| 033 | S. dysenteriae | AA-22239 | + | + |
| 034 | S. dysenteriae | AA-22538 | + | + |
| 035 | S. dysenteriae | ATCC9361 | + | + |
| 036 | S. dysenteriae | ATCC9753 | + | + |
| 037 | S. dysenteriae | ATCC11456a | + | + |
| 038 | S. dysenteriae | ATCC13313 | + | + |
| 039 | S. dysenteriae | ATCC23351 | + | + |
| 040 | S. dysenteriae | ATCC29027 | + | + |
| 041 | S. dysenteriae | ATCC29028 | + | + |
| 042 | S. flexneri | TUMD7 | − | − |
| 043 | S. flexneri | TUMD8 | − | − |
| 044 | S. flexneri | TUMD9 | + | + |
| 045 | S. flexneri | TUMD10 | − | − |
| 046 | S. flexneri | TUMD11 | − | − |
| 047 | S. flexneri | TUMD12 | + | + |
| 048 | S. flexneri | TUMD13 | + | + |
| 049 | S. flexneri | TUMD14 | − | − |
| 050 | S. flexneri | TUMD15 | + | + |
| 051 | S. flexneri | TUMD16 | − | − |
| 052 | S. flexneri | TUMD17 | − | − |
| 053 | S. flexneri | TUMD18 | − | − |
| 054 | S. flexneri | TUMD19 | + | + |
| 055 | S. flexneri | TUMD20 | − | − |
| 056 | S. flexneri | TUMD21 | − | − |
| 057 | S. flexneri | TUMD22 | − | − |
| 058 | S. flexneri | TUMD23 | − | − |
| 059 | S. flexneri | TUMD24 | + | + |
| 060 | S. flexneri | TUMD25 | − | − |
| 061 | S. flexneri | TUMD26 | − | − |
| 062 | S. flexneri | TUMD27 | − | − |
| 063 | S. flexneri | TUMD28 | − | − |
| 064 | S. flexneri | TUMD29 | − | − |
| 065 | S. flexneri | TUMD30 | + | + |
| 066 | S. flexneri | TUMD31 | − | − |
| 067 | S. flexneri | TUMD32 | − | − |
| 068 | S. flexneri | TUMD33 | − | − |
| 069 | S. flexneri | TUMD34 | − | − |
| 070 | S. flexneri | TUMD35 | + | + |
| 071 | S. flexneri | TUMD36 | + | + |
| 072 | S. flexneri | TUMD38 | − | − |
| 073 | S. flexneri | TUMD39 | + | + |
| 074 | S. flexneri | TUMD40 | − | − |
| 075 | S. flexneri | TUMD41 | + | + |
| 076 | S. flexneri | TUMD42 | + | + |
| 077 | S. flexneri | TUMD43 | + | + |
| 078 | S. flexneri | TUMD44 | + | + |
| 079 | S. flexneri | TUMD45 | + | + |
| 080 | S. flexneri | TUMD46 | − | − |
| 081 | S. flexneri | TUMD47 | + | + |
| 082 | S. flexneri | TUMD48 | − | − |
| 083 | S. flexneri | TUMD49 | + | + |
| 084 | S. flexneri | TUMD50 | − | − |
| 085 | S. flexneri | TUMD51 | − | − |
| 086 | S. flexneri | TUMD52 | + | + |
| 087 | S. flexneri | TUMD53 | − | − |
| 088 | S. flexneri | TUMD54 | − | − |
| 089 | S. flexneri | TUMD55 | − | − |
| 090 | S. flexneri | TUMD56 | − | − |
| 091 | S. flexneri | TUMD57 | − | − |
| 092 | S. flexneri | TUMD58 | − | − |
| 093 | S. flexneri | TUMD59 | − | − |
| 094 | S. flexneri | TUMD60 | − | − |
| 095 | S. flexneri | TUMD61 | − | − |
| 096 | S. flexneri | Maramba 89-77 | − | − |
| 097 | S. flexneri | Maramba 89-95 | + | + |
| 098 | S. flexneri | Maramba 89-109a | − | − |
| 099 | S. flexneri | Maramba 89-119 | − | − |
| 100 | S. flexneri | Maramba 89-155 | − | − |
| 101 | S. flexneri | Maramba 89-164 | − | − |
| 102 | S. flexneri | Maramba 89-150 | + | + |
| 103 | S. flexneri | AA-22175 | − | − |
| 104 | S. flexneri | AA-22371 | − | − |
| 105 | S. flexneri | AA-22266 | + | + |
| 106 | S. flexneri | AA-22636 | + | + |
| 107 | S. flexneri | AA-22187 | − | − |
| 108 | S. flexneri | AA-22170 | + | + |
| 109 | S. flexneri | AA-22367 | + | + |
| 110 | S. flexneri | AA-22316 | − | − |
| 111 | S. flexneri | AA-22265 | + | + |
| 112 | S. flexneri | AA-22296 | − | − |
| 113 | S. flexneri | AA-22312 | + | + |
| 114 | S. flexneri | AA-22246 | − | − |
| 115 | S. flexneri | AA-21981 | − | − |
| 116 | S. flexneri | AA-22097 | − | − |
| 117 | S. flexneri | AQ-7347 | + | + |
| 118 | S. flexneri | AQ-7348 | + | + |
| 119 | S. flexneri | AQ-7351 | − | − |
| 120 | S. flexneri | AQ-7360 | + | + |
| 121 | S. flexneri | AQ-7367 | + | + |
| 122 | S. flexneri | AQ-7372 | + | + |
| 123 | S. flexneri | AQ-7378 | − | − |
| 124 | S. flexneri | AQ-7379 | − | − |
| 125 | S. flexneri | AQ-7380 | − | − |
| 126 | S. flexneri | AQ-7385 | + | + |
| 127 | S. flexneri | AQ-7386 | − | − |
| 128 | S. flexneri | AQ-7390 | − | − |
| 129 | S. flexneri | AQ-7391 | + | + |
| 130 | S. flexneri | AQ-7393 | − | − |
| 131 | S. flexneri | AQ-7394 | − | − |
| 132 | S. flexneri | AQ-7398 | − | − |
| 133 | S. flexneri | AQ-7399 | − | − |
| 134 | S. flexneri | AQ-7400 | − | − |
| 135 | S. flexneri | AQ-7402 | − | − |
| 136 | S. flexneri | AQ-7407 | − | − |
| 137 | S. flexneri | AQ-7408 | − | − |
| 138 | S. flexneri | AQ-7411 | + | + |
| 139 | S. flexneri | AQ-7416 | + | + |
| 140 | S. flexneri | AQ-7417 | + | + |
| 141 | S. flexneri | AQ-7418 | + | + |
| 142 | S. flexneri | AQ-7423 | + | + |
| 143 | S. flexneri | AQ-7424 | − | − |
| 144 | S. flexneri | AQ-7426 | + | + |
| 145 | S. flexneri | AQ-7427 | − | − |
| 146 | S. flexneri | Manila 89-164 | − | − |
| 147 | S. flexneri | Manila 89-177 | − | − |
| 148 | S. flexneri | Manila 89-209 | − | − |
| 149 | S. flexneri | Manila 89-210 | + | + |
| 150 | S. flexneri | Manila 89-229 | + | + |
| 151 | S. flexneri | Manila 89-230 | − | − |
| 152 | S. flexneri | Manila 89-231 | + | + |
| 153 | S. flexneri | Manila 89-232 | + | + |
| 154 | S. flexneri | Manila 89-233 | − | − |
| 155 | S. flexneri | Manila 89-273 | + | + |
| 156 | S. flexneri | Manila 89-328 | + | + |
| 157 | S. flexneri | Manila 89-333 | + | + |
| 158 | S. flexneri | Manila 89-365 | + | + |

TABLE 5-continued

| No | Strains | | CH test* | Primer 5 + 6** |
|---|---|---|---|---|
| 159 | S. flexneri | Manila 89-274 | − | − |
| 160 | S. flexneri | Manila 89-436 | − | − |
| 161 | S. flexneri | Manila 89-438 | + | + |
| 162 | S. flexneri | Manila 89-443 | + | + |
| 163 | S. flexneri | Manila 89-444 | + | + |
| 164 | S. flexneri | Manila 89-450 | + | + |
| 165 | S. flexneri | Manila 89-480 | + | + |
| 166 | S. flexneri | Manila 89-483 | − | − |
| 167 | S. flexneri | Manila 89-486 | − | − |
| 168 | S. flexneri | Manila 89-498 | − | − |
| 169 | S. flexneri | Manila 89-499 | − | − |
| 170 | S. flexneri | Manila 89-503 | − | − |
| 171 | S. flexneri | Manila 89-509 | − | − |
| 172 | S. flexneri | Manila 89-532 | − | − |
| 173 | S. flexneri | Manila 89-539 | − | − |
| 174 | S. boydii | TUMD62 | − | − |
| 175 | S. boydii | TUMD63 | + | + |
| 176 | S. boydii | TUMD64 | + | + |
| 177 | S. boydii | TUMD65 | − | − |
| 178 | S. boydii | TUMD66 | + | + |
| 179 | S. boydii | TUMD67 | − | − |
| 180 | S. boydii | TUMD68 | − | − |
| 181 | S. boydii | AQ-7019 | − | − |
| 182 | S. boydii | AQ-7020 | − | − |
| 183 | S. boydii | AQ-7026 | − | − |
| 184 | S. boydii | AQ-7032 | + | + |
| 185 | S. boydii | AQ-7039 | + | + |
| 186 | S. boydii | AQ-7042 | + | + |
| 187 | S. boydii | AQ-7062 | + | + |
| 188 | S. boydii | AQ-7076 | − | − |
| 189 | S. boydii | AQ-7098 | + | + |
| 190 | S. boydii | AQ-7157 | + | + |
| 191 | S. boydii | AQ-7193 | − | − |
| 192 | S. boydii | AQ-7206 | − | − |
| 193 | S. boydii | AQ-7213 | + | + |
| 194 | S. boydii | AQ-7218 | + | + |
| 195 | S. boydii | AQ-7238 | + | + |
| 196 | S. boydii | AQ-7267 | − | − |
| 197 | S. boydii | AQ-7268 | + | + |
| 198 | S. boydii | AQ-7307 | + | + |
| 199 | S. boydii | AQ-7313 | − | − |
| 200 | S. boydii | AQ-7314 | − | − |
| 201 | S. boydii | AQ-7324 | − | − |
| 202 | S. boydii | AQ-7349 | + | + |
| 203 | S. boydii | AQ-7354 | − | − |
| 204 | S. boydii | AQ-7356 | − | − |
| 205 | S. boydii | AQ-7357 | + | + |
| 206 | S. boydii | AQ-7368 | + | + |
| 207 | S. boydii | AQ-7373 | + | + |
| 208 | S. boydii | AQ-7376 | − | − |
| 209 | S. boydii | AQ-7405 | + | + |
| 210 | S. boydii | AA-22562 | + | + |
| 211 | S. boydii | AA-22241 | − | − |
| 212 | S. boydii | AA-22610 | − | − |
| 213 | S. boydii | AA-20255 | + | + |
| 214 | S. boydii | AA-20211 | + | + |
| 215 | S. boydii | AA-21713 | − | − |
| 216 | S. boydii | AA-17405 | − | − |
| 217 | S. boydii | AA-22804 | − | − |
| 218 | S. boydii | AQ-7297 | + | + |
| 219 | S. sonnei | AQ-7366 | − | − |
| 220 | S. sonnei | AQ-7369 | + | + |
| 221 | S. sonnei | AQ-7371 | − | − |
| 222 | S. sonnei | AQ-7374 | − | − |
| 223 | S. sonnei | AQ-7375 | + | + |
| 224 | S. sonnei | AQ-7377 | + | + |
| 225 | S. sonnei | AQ-7381 | − | − |
| 226 | S. sonnei | AQ-7382 | − | − |
| 227 | S. sonnei | AQ-7383 | − | − |
| 228 | S. sonnei | AQ-7384 | − | − |
| 229 | S. sonnei | AQ-7387 | − | − |
| 230 | S. sonnei | AQ-7388 | + | + |
| 231 | S. sonnei | AQ-7389 | + | + |
| 232 | S. sonnei | AQ-7392 | + | + |
| 233 | S. sonnei | AQ-7395 | − | − |
| 234 | S. sonnei | AQ-7396 | − | − |
| 235 | S. sonnei | AQ-7397 | + | + |
| 236 | S. sonnei | AQ-7401 | + | + |
| 237 | S. sonnei | AQ-7406 | + | + |
| 238 | S. sonnei | AQ-7409 | − | − |
| 239 | S. sonnei | AQ-7410 | − | − |
| 240 | S. sonnei | AQ-7412 | − | − |
| 241 | S. sonnei | AQ-7413 | + | + |
| 242 | S. sonnei | AQ-7414 | − | − |
| 243 | S. sonnei | AQ-7415 | − | − |
| 244 | S. sonnei | AQ-7419 | + | + |
| 245 | S. sonnei | AQ-7420 | − | − |
| 246 | S. sonnei | AQ-7421 | + | + |
| 247 | S. sonnei | AQ-7422 | + | + |
| 248 | S. sonnei | AQ-7425 | − | − |
| 249 | S. sonnei | AA-22634 | + | + |
| 250 | S. sonnei | AA-22677 | + | + |
| 251 | S. sonnei | AA-18306 | − | − |
| 252 | S. sonnei | AA-22067 | − | − |
| 253 | S. sonnei | AA-22870 | − | − |
| 254 | S. sonnei | TUMD69 | + | + |
| 255 | S. sonnei | TUMD70 | − | − |
| 256 | S. sonnei | TUMD71 | − | − |
| 257 | S. sonnei | TUMD72 | − | − |
| 258 | S. sonnei | TUMD73 | + | + |
| 259 | S. sonnei | TUMD74 | − | − |
| 260 | S. sonnei | TUMD75 | + | + |
| 261 | S. sonnei | TUMD76 | − | − |
| 262 | S. sonnei | TUMD77 | − | − |
| 263 | S. sonnei | TUMD78 | + | + |
| 264 | S. sonnei | TUMD79 | − | − |
| 265 | S. sonnei | TUMD80 | − | − |
| 266 | S. sonnei | TUMD81 | + | + |
| 267 | S. sonnei | TUMD82 | − | − |
| 268 | S. sonnei | TUMD83 | − | − |
| 269 | S. sonnei | TUMD84 | − | − |
| 270 | S. sonnei | TUMD85 | − | − |
| 271 | S. sonnei | TUMD86 | − | − |
| 272 | S. sonnei | TUMD87 | − | − |
| 273 | S. sonnei | TUMD88 | − | − |
| 274 | S. sonnei | TUMD89 | − | − |
| 275 | S. sonnei | TUMD90 | + | + |
| 276 | S. sonnei | TUMD91 | − | − |
| 277 | S. sonnei | TUMD92 | + | + |
| 278 | S. sonnei | TUMD93 | + | + |
| 279 | S. sonnei | TUMD94 | + | + |
| 280 | S. sonnei | TUMD95 | − | − |
| 281 | S. sonnei | TUMD96 | − | − |
| 282 | S. sonnei | TUMD97 | − | − |
| 283 | S. sonnei | TUMD98 | − | − |
| 284 | S. sonnei | TUMD99 | − | − |
| 285 | S. sonnei | TUMD100 | − | − |
| 286 | S. sonnei | TUMD101 | − | − |
| 287 | S. sonnei | TUMD102 | + | + |
| 288 | S. sonnei | TUMD103 | + | + |
| 289 | S. sonnei | TUMD104 | + | + |
| 290 | S. sonnei | TUMD105 | + | + |
| 291 | S. sonnei | TUMD106 | − | − |
| 292 | S. sonnei | TUMD107 | + | + |
| 293 | S. sonnei | TUMD108 | − | − |
| 294 | S. sonnei | TUMD109 | + | + |
| 295 | S. sonnei | TUMD110 | − | − |
| 296 | S. sonnei | TUMD111 | + | + |
| 297 | S. sonnei | TUMD112 | − | − |
| 298 | S. sonnei | TUMD113 | + | + |
| 299 | S. sonnei | TUMD114 | + | + |
| 200 | S. sonnei | TUMD115 | − | − |
| 301 | S. sonnei | TUMD116 | − | − |
| 302 | S. sonnei | TUMD117 | − | − |
| 303 | S. sonnei | TUMD118 | + | + |
| 304 | S. sonnei | TUMD119 | + | + |
| 305 | S. sonnei | TUMD120 | + | + |
| 306 | S. sonnei | TUMD121 | − | − |
| 307 | S. sonnei | TUMD122 | − | − |
| 308 | S. sonnei | TUMD123 | + | + |
| 309 | S. sonnei | TUMD124 | + | + |
| 310 | S. sonnei | TUMD125 | | |

TABLE 5-continued

| No | Strains | | CH test* | Primer 5 + 6** |
|---|---|---|---|---|
| 311 | S. sonnei | TUMD126 | + | + |
| 312 | S. sonnei | TUMD127 | − | − |
| 313 | S. sonnei | TUMD128 | − | − |
| 314 | S. sonnei | Maramba 89-154 | + | + |
| 315 | S. sonnei | Maramba 89-161 | − | − |
| 316 | S. sonnei | Manila 89-342 | − | − |
| 317 | S. sonnei | Manila 89-445 | + | + |
| 318 | E. coli | DMR6 | + | + |
| 319 | E. coli | DMR78 | + | + |
| 320 | E. coli | DMR79 | − | − |
| 321 | E. coli | AQ8001 | − | − |
| 322 | E. coli | AQ8003 | + | + |
| 323 | E. coli | AQ8004 | − | − |
| 324 | E. coli | AQ8008 | + | + |
| 325 | E. coli | AQ8010 | + | + |
| 326 | E. coli | AQ8011 | + | + |
| 327 | E. coli | AQ8012 | + | + |
| 328 | E. coli | AQ8013 | − | − |
| 329 | E. coli | AQ8016 | + | + |
| 330 | E. coli | AQ8019 | + | + |
| 331 | E. coli | AQ8022 | + | + |
| 332 | E. coli | AQ8024 | − | − |
| 333 | E. coli | AQ8025 | + | + |
| 334 | E. coli | AQ8027 | − | − |
| 335 | E. coli | AQ8028 | + | + |
| 336 | E. coli | AQ8029 | + | + |
| 337 | E. coli | AQ8031 | + | + |
| 338 | E. coli | AQ8033 | − | − |
| 339 | E. coli | AQ8036 | − | − |
| 340 | E. coli | AQ8044 | + | + |
| 341 | E. coli | PE660 | + | + |

[Experiment 2]

To determine whether the results obtained in Experiment 1 are specific to the invE gene, DNAs of clinically important pathogenic bacteria other than Shigella species and EIEC are examined with the primers of the present invention. The same procedure as used in Experiment 1 is followed, except for the procedure of preparation of specimens.

Preparation of Specimens

Each strain listed in Table 6 is treated in the same manner as in Experiment 2 of Example 1.

Results

Table 6 shows the results of the test using the combination of primers of the present invention. This combination of primers does not amplify any DNAs of pathogenic bacteria other than Shigella species and EIEC. It can therefore be concluded that the oligonucleotide primers of the present invention selectively react with DNAs of the bacteria having the invE gene.

TABLE 6

| No | Strains | | PCR |
|---|---|---|---|
| 01 | Bacillus cereus | ATCC14579 | − |
| 02 | Bacillus Subtilis | JCM1465 | − |
| 03 | Staphylococcus aureus | JCM2413 | − |
| 04 | Staphylococcus epidermidis | JCM2414 | − |
| 05 | Salmonella typhimurium | IFO12529 | − |
| 06 | Salmonella enteritidis | IFO3163 | − |
| 07 | Clostridium perfringens | ATCC12917 | − |
| 08 | Vibrio cholerae | ATCC25872 | − |
| 09 | Vibrio cholerae type Ogawa | ATCC9458 | − |
| 10 | Vibrio cholerae type Inaba | ATCC9459 | − |
| 11 | Vibrio fluvialis | JCM3752 | − |
| 12 | Campylobacter jejuni | JCM2013 | − |
| 13 | Campylobacter coli | JCM2529 | − |
| 14 | Escherichia coli | JCM1649 | − |
| 15 | Yersinia enterocolitica | ATCC9610 | − |
| 16 | Corynebacterium diphtheriae | JCM13 | − |
| 17 | Peptostreptococcus anaerobius | ATCC273 | − |
| 18 | Bacteroides flagilis | ATCC23745 | − |
| 19 | Bacteroides vulgatus | JCM5826 | − |
| 20 | Enterococcus faecalis | JCM5803 | − |
| 21 | Klebsiella pneumoniae | JCM1662 | − |
| 22 | Proteus vulgaris | JCM1668 | − |
| 23 | Citrobacter freundii | ATCC33128 | − |
| 24 | Streptococcus pyogenes | ATCC12344 | − |
| 25 | Streptococcus pneumoniae | ATCC33400 | − |
| 26 | Elaemophilis influenzae | ATCC33391 | − |
| 27 | Proteus mirabilis | ATCC29906 | − |
| 28 | Neisseria meningitidis | ATCC13077 | − |
| 29 | Neisseria gonorthoeae | ATCC19424 | − |
| 30 | Listeria monocytogenes | ATCC15313 | − |
| 31 | Lactobacillus acidophilus | JCM1132 | − |
| 32 | Bifidobacterium adolescentis | JCM1275 | − |
| 33 | Fusobacterium nucleatum | ATCC25586 | − |
| 34 | Propionibacterium acnes | ATCC6919 | − |
| 35 | Veillonella atypica | ATCC17744 | − |
| 36 | Pseudomonas aeruginosa | IFO12689 | − |
| 37 | Human placental DNA | | − |

Example 4

Detection of Salmonella Species Having the araC Gene

[Experiment 1]

Preparation of Specimens

As listed in Tables 7-1 to 7-6, the 133 various Salmonella species isolated from the patients and food samples are used. The details are as follows: 67 strains of Salmonella typhimurium, 1 of Salmonella havana, 2 of Salmonella oranienburg, 3 of Salmonella london, 3 of Salmonella senftenberg, 4 of Salmonella blockley, 3 of Salmonella agona, 4 of Salmonella infantis, 14 of Salmonella litchfield, 6 of Salmonella enteritidis, 13 of Salmonella thompson, 6 of Samonella paratyphi B, 2 of Salmonella montevideo, 1 of Salmonella gallinarum, 1 of Salmonella choleraesuis, 1 of Salmonella derby, 1 of Salmonella give and 1 of Salmonella deidelberg. Each strain is inoculated to an appropriate medium, and subjected to overnight culture at 37° C. under aerobic conditions. Each culture broth is diluted with TE buffer, and heated at 95° C. for 10 minutes, followed by centrifugation. The supernatants are used as specimens.

Synthesis of Primers

As primers for amplifying the araC gene of Salmonella typhimurium, the above-described oligonucleotides SEQ ID NO:7 to SEQ ID NO:11 are selected based upon the known base sequence of the araC gene [Horwitz, A. H., et al., Gene 14, 309–319(1981); Clarke, P., et al., Gene 18, 157–163 (1982); Lee, J. -H., et al., Gene 46, 113–121 (1986)], and chemically synthesized by the same method as in Experiment 1 of Example 1.

PCR

PCR is carried out under the same reaction conditions as in Example 1 except that any one of the following oligonucleotide combinations is used:

Primer (1)+primer (2)=

Oligonucleotide SEQ ID NO:7+Oligonucleotide SEQ ID NO:8;

Oligonucleotide SEQ ID NO:9+Oligonucleotide SEQ ID NO:10; and

Oligonucleotide SEQ ID NO:11+Oligonucleotide SEQ ID NO:8.

Detection

Agarose Gel Electrophoresis

The same procedure as in Example 1 is followed.

Results

The base sequence of the araC gene of *Salmonella typhimurium* has already been determined. This base sequence is thought to be common to all Salmonella species. The length of the nucleotide fragments amplified by PCR using the oligonucleotides of the present invention as primers can easily be estimated. Specifically, when oligonucleotides SEQ ID NO: 7 and SEQ ID NO: 8 of the present invention are used in combination, a nucleotide fragment of 361 bases (or a nucleotide duplex of 361 base pairs) is amplified. Similarly, the combination of SEQ ID NO: 9 and SEQ ID NO:10, and that of SEQ ID NO:11 and SEQ ID NO:8 amplify nucleotide fragment of 493 bases and that of 334 bases, respectively. When these estimations accord with the length of the amplified nucleotide fragments, it is judged that PCR using the combination of primers accurately amplifies the target region in the araC gene, and that the bacterial strain in the specimen has the araC gene. Tables 7-1 to 7-6 shows the results of the detection of the araC gene in Salmonella species. As obvious from Tables 7-1 to 7-6, the araC gene of Salmonella species are detected with high accuracy by using the oligonucleotide primers of the present invention.

TABLE 7

| | | | Combination of primers* | | |
|---|---|---|---|---|---|
| No | Strains | | 7 + 8** | 9 + 10** | 11 + 8** |
| 001 | *Salmonella typhimurium* | 56-1 | + | + | + |
| 002 | *Salmonella typhimurium* | 56-2 | + | + | + |
| 003 | *Salmonella typhimurium* | 56-3 | + | + | + |
| 004 | *Salmonella typhimurium* | 56-4 | + | + | + |
| 005 | *Salmonella typhimurium* | 56-5 | + | + | + |
| 006 | *Salmonella typhimurium* | 56-6 | + | + | + |
| 007 | *Salmonella typhimurium* | 56-7 | + | + | + |
| 008 | *Salmonella typhimurium* | 56-11 | + | + | + |
| 009 | *Salmonella typhimurium* | 56-12 | + | + | + |
| 010 | *Salmonella typhimurium* | 56-13 | + | + | + |
| 011 | *Salmonella typhimurium* | 56-17 | + | + | + |
| 012 | *Salmonella typhimurium* | 56-18 | + | + | + |
| 013 | *Salmonella typhimurium* | 56-19 | + | + | + |
| 014 | *Salmonella typhimurium* | 56-20 | + | + | + |
| 015 | *Salmonella typhimurium* | 56-21 | + | + | + |
| 016 | *Salmonella typhimurium* | 56-22 | + | + | + |
| 017 | *Salmonella typhimurium* | 56-23 | + | + | + |
| 018 | *Salmonella typhimurium* | 56-25 | + | + | + |
| 019 | *Salmonella typhimurium* | 56-26 | + | + | + |
| 020 | *Salmonella typhimurium* | 56-27 | + | + | + |
| 021 | *Salmonella typhimurium* | 56-30 | + | + | + |
| 022 | *Salmonella typhimurium* | 56-31 | + | + | + |
| 023 | *Salmonella typhimurium* | 56-32 | + | + | + |
| 024 | *Salmonella typhimurium* | 57-3 | + | + | + |
| 025 | *Salmonella typhimurium* | 57-4 | + | + | + |
| 026 | *Salmonella typhimurium* | 57-5 | + | + | + |
| 027 | *Salmonella typhimurium* | 57-6 | + | + | + |
| 028 | *Salmonella typhimurium* | 57-7 | + | + | + |
| 029 | *Salmonella typhimurium* | 57-9 | + | + | + |
| 030 | *Salmonella typhimurium* | 57-10 | + | + | + |
| 031 | *Salmonella typhimurium* | 57-11 | + | + | + |
| 032 | *Salmonella typhimurium* | 57-19 | + | + | + |
| 033 | *Salmonella typhimurium* | 57-20 | + | + | + |
| 034 | *Salmonella typhimurium* | 59-26 | + | + | + |
| 035 | *Salmonella typhimurium* | 59-27 | + | + | + |
| 036 | *Salmonella typhimurium* | 59-28 | + | + | + |
| 037 | *Salmonella typhimurium* | 59-54 | + | + | + |
| 038 | *Salmonella typhimurium* | 59-55 | + | + | + |
| 039 | *Salmonella typhimurium* | 59-56 | + | + | + |
| 040 | *Salmonella typhimurium* | 59-57 | + | + | + |
| 041 | *Salmonella typhimurium* | 59-58 | + | + | + |
| 042 | *Salmonella typhimurium* | 60-5 | + | + | + |
| 043 | *Salmonella typhimurium* | 60-6 | + | + | + |
| 044 | *Salmonella typhimurium* | 60-7 | + | + | + |
| 045 | *Salmonella typhimurium* | 60-13 | + | + | + |
| 046 | *Salmonella typhimurium* | 61-1 | + | + | + |
| 047 | *Salmonella typhimurium* | 61-16 | + | + | + |
| 048 | *Salmonella typhimurium* | 62-1 | + | + | + |
| 049 | *Salmonella typhimurium* | 62-2 | + | + | + |
| 050 | *Salmonella typhimurium* | 62-3 | + | + | + |
| 051 | *Salmonella typhimurium* | 62-4 | + | + | + |
| 052 | *Salmonella typhimurium* | 62-5 | + | + | + |
| 053 | *Salmonella typhimurium* | 62-6 | + | + | + |
| 054 | *Salmonella typhimurium* | 63-6 | + | + | + |
| 055 | *Salmonella typhimurium* | 63-7 | + | + | + |
| 056 | *Salmonella typhimurium* | 63-8 | + | + | + |
| 057 | *Salmonella typhimurium* | 63-9 | + | + | + |
| 058 | *Salmonella typhimurium* | 89-1 | + | + | + |

TABLE 7-continued

| No | Strains | | Combination of primers* | | |
|---|---|---|---|---|---|
| | | | 7 + 8** | 9 + 10** | 11 + 8** |
| 059 | Salmonella typhimurium | 89-2 | + | + | + |
| 060 | Salmonella typhimurium | IFO12529 | + | + | + |
| 061 | Salmonella typhimurium | IFO13245 | + | + | + |
| 062 | Salmonella typhimurium | IFO14193 | + | + | + |
| 063 | Salmonella typhimurium | IFO14194 | + | + | + |
| 064 | Salmonella typhimurium | IFO14209 | + | + | + |
| 065 | Salmonella typhimurium | IFO14210 | + | + | + |
| 066 | Salmonella typhimurium | IFO14211 | + | + | + |
| 067 | Salmonella typhimurium | IFO14212 | + | + | + |
| 068 | Salmonella litchfield | 56-8 | + | + | + |
| 069 | Salmonella litchfield | 59-25 | + | + | + |
| 070 | Salmonella litchfield | 53-22 | + | + | + |
| 071 | Salmonella litchfield | 53-23 | + | + | + |
| 072 | Salmonella litchfield | 53-24 | + | + | + |
| 073 | Salmonella litchfield | 54-5 | + | + | + |
| 074 | Salmonella litchfield | 54-6 | + | + | + |
| 075 | Salmonella litchfield | 55-3 | + | + | + |
| 076 | Salmonella litchfield | 55-4 | + | + | + |
| 077 | Salmonella litchfield | 55-6 | + | + | + |
| 078 | Salmonella litchfield | 55-7 | + | + | + |
| 079 | Salmonella litchfield | 55-8 | + | + | + |
| 080 | Salmonella litchfield | 55-12 | + | + | + |
| 081 | Salmonella litchfield | 55-13 | + | + | + |
| 082 | Salmonella thompson | 61-2 | + | + | + |
| 083 | Salmonella thompson | 61-3 | + | + | + |
| 084 | Salmonella thompson | 61-4 | + | + | + |
| 085 | Salmonella thompson | 61-17 | + | + | + |
| 086 | Salmonella thompson | 61-18 | + | + | + |
| 087 | Salmonella thompson | 52-3 | + | + | + |
| 088 | Salmonella thompson | 52-4 | + | + | + |
| 089 | Salmonella thompson | 53-5 | + | + | + |
| 090 | Salmonella thompson | 53-6 | + | + | + |
| 091 | Salmonella thompson | 53-7 | + | + | + |
| 092 | Salmonella thompson | 53-20 | + | + | + |
| 093 | Salmonella thompson | 53-21 | + | + | + |
| 094 | Salmonella thompson | NIAH1230 | + | + | + |
| 095 | Salmonella enteritidis | 59-36 | + | + | + |
| 096 | Salmonella enteritidis | 59-37 | + | + | + |
| 097 | Salmonella enteritidis | 59-38 | + | + | + |
| 098 | Salmonella enteritidis | 53-1 | + | + | + |
| 099 | Salmonella enteritidis | 53-2 | + | + | + |
| 100 | Salmonella enteritidis | IFO3313 | + | + | + |
| 101 | Salmonella paratyphi B | 61-19 | + | + | + |
| 102 | Salmonella paratyphi B | 61-20 | + | + | + |
| 103 | Salmonella paratyphi B | 61-21 | + | + | + |
| 104 | Salmonella paratyphi B | 63-1 | + | + | + |
| 105 | Salmonella paratyphi B | 63-2 | + | + | + |
| 106 | Salmonella paratyphi B | 63-3 | + | + | + |
| 107 | Salmonella blockley | 58-55 | + | + | + |
| 108 | Salmonella blockley | 58-56 | + | + | + |
| 109 | Salmonella blockley | 58-57 | + | + | + |
| 110 | Salmonella blockley | NIAH1197 | + | + | + |
| 111 | Salmonella infantis | 59-20 | + | + | + |
| 112 | Salmonella infantis | 59-21 | + | + | + |
| 113 | Salmonella infantis | 59-22 | + | + | + |
| 114 | Salmonella infantis | NIAH1218 | + | + | + |
| 115 | Salmonella agona | 59-1 | + | + | + |
| 116 | Salmonella agona | 59-2 | + | + | + |
| 117 | Salmonella agona | 59-3 | + | + | + |
| 118 | Salmonella london | 58-7 | + | + | + |
| 119 | Salmonella london | 58-8 | + | + | + |
| 120 | Salmonella london | 58-9 | + | + | + |
| 121 | Salmonella senftenberg | 58-27 | + | + | + |
| 122 | Salmonella senftenberg | 58-28 | + | + | + |
| 123 | Salmonella senftenberg | 58-29 | + | + | + |
| 124 | Salmonella oranienburg | 57-1 | + | + | + |
| 125 | Salmonella oranienburg | 57-2 | + | + | + |
| 126 | Salmonella montevideo | 54-4 | + | + | + |
| 127 | Salmonella montevideo | NIAH1221 | + | + | + |
| 128 | Salmonella gallinarum | IFO3163 | + | + | + |
| 129 | Salmonella choleraesuis | NIAH1198 | + | + | + |
| 130 | Salmonella derby | NIAH1199 | + | + | + |
| 131 | Salmonella give | NIAH1214 | + | + | + |

TABLE 7-continued

|  |  |  | Combination of primers* | | |
|---|---|---|---|---|---|
| No | Strains |  | 7 + 8** | 9 + 10** | 11 + 8** |
| 132 | *Salmonella havana* | 56-44 | + | + | + |
| 133 | *Salmonella heiderberg* | NIAH1216 | + | + | + |

Note)
*+DNA of estimated length is amplified.
N: DNA of not-estimated length is amplified.
−DNA is not amplified.
**Numerals refer to SEQ ID NOs.

[Experiment 2]

To determine whether the results obtained in Experiment 1 are specific to the araC gene of Salmonella species, DNAs of clinically important diarrheal bacteria other than Salmonella species and other pathogenic bacteria are examined with the primers of the present invention. In particular, differentiation between Salmonella species and Citrobacter species, which has been difficult by conventional methods, is carefully examined.

The same procedure as used in Experiment 1 is followed, except for the procedure of preparation of specimens.

Preparation of Specimens

*Clostridium perfringens, Campylobacter jejuni, Campylobacter coli, Bacteroides fragilis, Bacteroides vulgatus, Lactobacillus acidophilus* and *Bifidobacterium adolescentis* are cultured at 37° C. under anaeorbic conditions, while *Neisseria gonorrhoeae* and *Neisseria meningitidis* are cultured in the presence of 3–10% $CO_2$.

Human placenta DNA, at a concentration of 1 μg/ml, is subjected to PCR in the same manner as above.

Results

Tables 8-1 to 8-3 shows the results of the test using the combinations of the primers of the present invention. These combinations of primers do not amplify any DNAs of bacterial strains other than Salmonella species or DNAs of human placenta. It is of particular importance that the combinations of the primers of the present invention do not amplify any DNAs of Citrobacter species which are closely akin to and hardly differentiated from Salmonella species. It can therefore be concluded that the oligonucleotide primers of the present invention selectively react with the DNAs of Salmonella species, with high reliability.

TABLE 8

|  |  |  | Combination of primers* | | |
|---|---|---|---|---|---|
| No | Strains |  | 7 + 8** | 9 + 10** | 11 + 8** |
| 01 | *Bacillus cereus* | ATCC14579 | − | − | − |
| 02 | *Bacillus subtilis* | JCM1465 | − | − | − |
| 03 | *Staphylococcus aureus* | JCM2413 | − | − | − |
| 04 | *Staphylococcus epidermidis* | JCM2414 | − | − | − |
| 05 | *Clostridium perfringens* | ATCC12917 | − | − | − |
| 06 | *Vibrio cholerae* | ATCC25872 | − | − | − |
| 07 | *Vibrio cholerae* type Ogawa | ATCC9458 | − | − | − |
| 08 | *Vibrio cholerae* type Inaba | ATCC9459 | − | − | − |
| 09 | *Vibrio cholerae* | 61H-151 | − | − | − |
| 10 | *Vibrio parahaemolyticus* | WF-1 | − | − | − |
| 11 | *Vibrio fluvialis* | JCM3752 | − | − | − |
| 12 | *Campylobacter jejuni* | JCM2013 | − | − | − |
| 13 | *Campylobacter coli* | JCM2529 | − | − | − |
| 14 | *Escherichia coli* | JCM1649 | − | − | − |
| 15 | *Escherichia coli* | H10407 | − | − | − |
| 16 | *Escherichia coli* | WHO 3 | − | − | − |
| 17 | *Escherichia coli* | WHO 47 | − | − | − |
| 18 | *Escherichia coli* | T-1 | − | − | − |
| 19 | *Escherichia coli* | T-40 | − | − | − |
| 20 | *Yersinia enterocolitica* | ATCC9610 | − | − | − |
| 21 | *Shigella dysenteriae* | ATCC9361 | − | − | − |
| 22 | *Shigella boydii* | ATCC9210 | − | − | − |
| 23 | *Shigella flexneri* | ATCC11836 | − | − | − |
| 24 | *Shigella sonnei* | ATCC9290 | − | − | − |
| 25 | *Bacteroides flagilis* | ATCC23745 | − | − | − |
| 26 | *Bacteroides vulgatus* | JCM5826 | − | − | − |
| 27 | *Proteus vulgaris* | JCM1668 | − | − | − |
| 28 | *Proteus mirabilis* | ATCC29906 | − | − | − |
| 29 | *Streptococcus pyogenes* | ATCC12344 | − | − | − |
| 30 | *Streptococcus pneumoniae* | ATCC33400 | − | − | − |
| 31 | *Heamophilis influenzae* | ATCC33391 | − | − | − |
| 32 | *Klebsiella pneumoniae* | JCM1662 | − | − | − |
| 33 | *Neisseria gonorrheae* | ATCC19424 | − | − | − |
| 34 | *Neisseria meningitidis* | ATCC13O77 | − | − | − |
| 35 | *Listeria monocytogenes* | ATCC15313 | − | − | − |
| 36 | *Lactobacillus acidophilus* | JCM1132 | − | − | − |
| 37 | *Bifidobacterium adolescentis* | JCM1275 | − | − | − |

TABLE 8-continued

| | | Combination of primers* | | |
|---|---|---|---|---|
| No | Strains | | 7 + 8** | 9 + 10** | 11 + 8** |
| 38 | *Fusobacterium nucleatum* | ATCC25586 | – | – | – |
| 39 | *Propionibacterium acnes* | ATCC6919 | – | – | – |
| 40 | *Veillonella atypica* | ATCC17744 | – | – | – |
| 41 | *Pseudomonas aeruginosa* | IFO12689 | – | – | – |
| 42 | *Corynebacterium diphtheriae* | JCM1310 | – | – | – |
| 43 | *Peptostreptococcus anaerobius* | ATCC27337 | – | – | – |
| 44 | *Citrobacter freundii* | ATCC6750 | – | – | – |
| 45 | *Citrobacter freundii* | ATCC6879 | – | – | – |
| 46 | *Citrobacter freundii* | ATCC8090 | – | – | – |
| 47 | *Citrobacter freundii* | ATCC8454 | – | – | – |
| 48 | *Citrobacter freundii* | ATCC10053 | – | – | – |
| 49 | *Citrobacter freundii* | ATCC10625 | – | – | – |
| 50 | *Citrobacter freundii* | ATCC10787 | – | – | – |
| 51 | *Citrobacter freundii* | ATCC11102 | – | – | – |
| 52 | *Citrobacter freundii* | ATCC11811 | – | – | – |
| 53 | *Citrobacter freundii* | ATCC29063 | – | – | – |
| 54 | *Citrobacter freundii* | ATCC29219 | – | – | – |
| 55 | *Citrobacter freundii* | ATCC29220 | – | – | – |
| 56 | *Citrobacter freundii* | ATCC29221 | – | – | – |
| 57 | *Citrobacter freundii* | ATCC29222 | – | – | – |
| 58 | *Citrobacter freundii* | ATCC29935 | – | – | – |
| 59 | *Citrobacter freundii* | ATCC33128 | – | – | – |
| 60 | *Citrobacter amalonaticus* | ATCC25405 | – | – | – |
| 64 | *Citrobacter amalonaticus* | ATCC25406 | – | – | – |
| 64 | *Citrobacter amalonaticus* | ATCC25407 | – | – | – |
| 65 | *Citrobacter diversus* | ATCC27156 | – | – | – |
| 65 | *Citrobacter diversus* | ATCC29223 | – | – | – |
| 65 | *Citrobacter diversus* | ATCC29224 | – | – | – |
| 66 | *Citrobacter diversus* | ATCC29225 | – | – | – |
| 67 | *Citrobacter diversus* | ATCC29936 | – | – | – |

Note)
* +DNA of estimated length is amplified.
N: DNA of not-estimated length is amplified.
–DNA is not amplified.
**Numerals refer to SEQ ID NOs.

Example 5

Detection of EHEC (VTEC) Having the VT1 Gene
[Experiment 1]
Preparation of Specimens The same procedure as used in Example 1 is followed except that 320 strains of EHEC (VTEC) strains.

Synthesis of Primers

As primers for amplifying the VT1 gene of EHEC (VTEC), the above-described oligonucleotides SEQ ID NO:12 and SEQ ID NO:13 are selected based upon the known base sequence of the VT1 gene [Takao T., et al., Microb. Pathog., 5, 357–369(1988)]. These oligonucleotides are chemically synthesized by the same method as in Experiment 1 of Example 1.

PCR

PCR is carried out under the same reaction conditions as in Example 1 except that the following oligonucleotide combination is used:
Primer (1)+primer (2)=
Oligonucleotide SEQ ID NO:12+Oligonucleotide SEQ ID NO:13

Detection

Agarose Gel Electrophoresis

The same procedure as in Example 1 is followed.

Colony Hybridization Test

A colony hybridization test is carried out using an oligonucleotide probe specific to the VT1 gene and that specific to the VT2 gene according to the procedure described by Grunstein [Grunstein, M. and Hogness, D., Proc. Natl. Acad. Sci., 72, 3961(1975)].

Results

The base sequence of the VT1 gene of EHEC(VTEC) has already been determined. Therefore, the length of the nucleotide fragments amplified by PCR using the oligonucleotides of the present invention as primers can easily be estimated. Specifically, when the oligonucleotides SEQ ID NO:12 and SEQ ID NO:13 of the present invention are used in combination, a nucleotide fragment of 349 bases (or a nucleotide duplex of 349 base pairs) should be amplified. When this estimation accords with the length of the amplified nucleotide fragment, it is judged that PCR using the combination of primers accurately amplifies the target region in the VT1 gene, and that the bacterial strain in the specimen has the VT1 gene. The results obtained from the agarose gel electrophoresis and from the colony hybridization test for 320 test strains are given in Table 9. Table 9 shows that PCR using the primers of the present invention amplifies only DNAs of the strains which give a positive result for the VT1 gene in the colony hybridization test, and that it does not amplify the DNA of the VT1 negative strains. This indicates that PCR using the primers of the present invention is capable of accurately amplifying the VT1 gene and that EHEC(VTEC) having the VT1 gene can be detected with high accuracy by using the oligonucleotides of the present invention.

TABLE 9

Accuracy of the primers

| | Results of colony hybridization test | | | |
|---|---|---|---|---|
| | Positive for VT 1 gene | Positive for VT 2 gene | Positive for both VT 1 and VT 2 genes | Negative for both VT 1 and VT 2 genes |
| Results of PCR | | | | |
| Positive | 39 | 0 | 53 | 0 |
| Negative | 0 | 185 | 0 | 43 |

[Experiment 2]

To determine whether the results obtained in Experiment 1 are specific to EHEC (VTEC) having the VT1 gene, the DNAs of clinically important pathogenic bacteria other than EHEC (VTEC) are examined with the primers of the present invention. The same procedure as used in Experiment 1 is followed, except for the procedure of preparation of specimens.

Preparation of Specimens

Each strain listed in Table 10 is treated in the same manner as in Experiment 2 of Example 1. Among strains listed in Table 10, the following strains are cultured under anaerobic conditions: *Clostridium perfringens, Campylobacter jejuni, Bacteroides fragilis, Bacteroides vulgatus* and *Lactobacillus acidophilus*.

Results

Table 10 shows the results from the test using the combinations of primers of the present invention. Although the combinations of primers do not amplify DNAs of any other strains than EHEC(VTEC) except for a certain type of Shigella species (*Shigella dysenteriae* type I).

It is well known that the differentiation between EHEC (VTEC) and *Shigella dysenteriae* is impossible because *Shigella dysenteriae* has the VT1 gene. It can therefore be concluded that the oligonucleotide primers of the present invention selectively react with the DNAs of the bacteria having the VT1 gene.

TABLE 10

Reactivity with un-targeted gene

| | | | Combination of primers | | | |
|---|---|---|---|---|---|---|
| No | Strains | | 12 + 13* | 14 + 15* | 16 + 18* | 17 + 18* |
| 1 | *Bacillus cereus* | ATCC 14579 | − | − | − | − |
| 2 | *B. subtilis* | JCM 1465 | − | − | − | − |
| 3 | *Staphylococcus aureus* | JCM 2413 | − | − | − | − |
| 4 | *S. epidermidis* | JCM 2414 | − | − | − | − |
| 5 | *Salmonella typhimurium* | IFO 12529 | − | − | − | − |
| 6 | *S. enteritidis* | IFO 3163 | − | − | − | − |
| 7 | *Clostridium perfringens* | ATCC 12917 | − | − | − | − |
| 8 | *Vibrio fluvialis* | JCM 3752 | − | − | − | − |
| 9 | *Campylobacter jejuni* | JCM 2013 | − | − | − | − |
| 10 | *C. coli* | JCM 2529 | − | − | − | − |
| 11 | *Escherichia coli* | JCM 1649 | − | − | − | − |
| 12 | *Yersinia enterocolitica* | ATCC 9610 | − | − | − | − |
| 13 | *Shigella dysenteriae* | ATCC 9361 | + | − | + | + |
| 14 | *S. flexneri* | ATCC 29903 | − | − | − | − |
| 15 | *S. sonnei* | ATCC 29930 | − | − | − | − |
| 16 | *Bacteroides fragilis* | ATCC 23745 | − | − | − | − |
| 17 | *B. vulgatus* | JCM 5826 | − | − | − | − |
| 18 | *Enterococcus faecalis* | JCM 5803 | − | − | − | − |
| 19 | *Klebsiella pneumoniae* | JCM 1662 | − | − | − | − |
| 20 | *Proteus vulgaris* | JCM 1668 | − | − | − | − |
| 21 | *Citrobacter freundii* | ATCC 33128 | − | − | − | − |
| 22 | *Streptococcus pyogenes* | ATCC 12344 | − | − | − | − |
| 23 | *S. pneumoniae* | ATCC 33400 | − | − | − | − |
| 24 | *Haemophilus influenzae* | ATCC 33391 | − | − | − | − |
| 25 | *Proteus mirabilis* | ATCC 29906 | − | − | − | − |
| 26 | *Neisseria gonorrhoeae* | ATCC 19424 | − | − | − | − |
| 27 | *N. meningitidis* | ATCC 13077 | − | − | − | − |
| 28 | *Listeria monocytogenes* | ATCC 15313 | − | − | − | − |
| 29 | *Lactobacillus acidophilus* | JCM 1132 | − | − | − | − |
| 30 | *Bifidobacterium adolescentis* | JCM 1275 | − | − | − | − |
| 31 | *Fusobacterium nucleatum* | ATCC 2558 | − | − | − | − |
| 32 | *Propionibacterium acnes* | ATCC 6919 | − | − | − | − |
| 33 | *Veillonella atypica* | ATCC 17744 | − | − | − | − |
| 34 | *Pseudomonas aeruginosa* | IFO 12689 | − | − | − | − |
| 35 | *Corynebacterium diphtheriae* | JCM 1310 | − | − | − | − |
| 36 | *Peptostreptococcus anaerobius* | ATCC 27337 | − | − | − | − |
| 37 | *Vibrio cholerae* | ATCC 25872 | − | − | − | − |
| 38 | *V. cholerae* type Ogawa | ATCC 9458 | − | − | − | − |
| 39 | *V. chalerae* type Inaba | ATCC 9459 | − | − | − | − |

Note)
*Numerals refer to SEQ ID NOs.
**+reactive
−nonreactive

Example 6

Detection of EHEC (VTEC) Having the VT2 Gene

[Experiment 1]

Preparation of Specimens

The same procedure as used in Experiment 1 of Example 5 is followed.

Synthesis of Primers

As primers for amplifying the VT2 gene of EHEC (VTEC) strains, the above-described oligonucleotides SEQ ID NO:14 and SEQ ID NO:15 are selected based upon the known base sequence of the VT2 gene [Jackson, M. P., et al., FEMS Microbio. Lett., 44, 109–114(1987)]. These oligonucleotides are chemically synthesized by the same method as in Example

PCR

PCR is carried out under the same reaction conditions as in Example 1 except that the following oligonucleotide combination is used:

Primer (1)+primer (2)=

Oligonucleotide SEQ ID NO:14+Oligonucleotide SEQ ID NO:15

Detection

Agarose Gel Electrophoresis

The same procedure as in Example 1 is followed.

Colony Hybridization Test

The same procedure as in Experiment 1 of Example 5 is followed.

Results

The base sequence of the VT2 gene of EHEC(VTEC) has already been determined. Therefore, the length of the nucleotide fragments amplified by PCR using the oligonucleotides of the present invention as primers can easily be estimated. Specifically, when oligonucleotides SEQ ID NO:14 and SEQ ID NO:15 of the present invention are used in combination, a nucleotide fragment of 404 bases (or a nucleotide duplex of 404 base pairs) should be amplified. When this estimation accords with the length of the amplified nucleotide fragment, it is judged that PCR using the combination of primers accurately amplifies the target region in the VT2 gene, and that the bacterial strain in the specimen has the VT2 gene. The results obtained from the agarose gel electrophoresis with 320 test strains and from the colony hybridization test are given in Table 11. PCR using the primers of the present invention amplifies only DNAs of the strains which give a result positive for the VT2 gene in the colony hybridization test, showing no amplification of the DNA of the VT2 negative strains. This indicates that PCR using the primers of the present invention is capable of accurately amplifying the VT2 gene and that EHEC(VTEC) having the VT2 gene can be detected with high accuracy by using the oligonucleotides of the present invention.

TABLE 11

| | Accuracy of the primers | | | |
|---|---|---|---|---|
| | Results of colony hybridization test | | | |
| | Positive for VT 1 gene | Positive for VT 2 gene | Positive for both VT 1 and VT 2 genes | Negative for both VT 1 and VT 2 genes |
| Results of PCR | | | | |
| Positive | 0 | 185 | 53 | 0 |
| Negative | 39 | 0 | 0 | 43 |

[Experiment 2]

To determine whether the results obtained in Experiment 1 are specific to EHEC (VTEC) having the VT2 gene, the DNAs of clinically important pathogenic bacteria other than EHEC (VTEC) are examined with the primers of the present invention. The same procedure as used in Experiment 2 of Example 5 is followed.

Results

Table 10 shows the results of the test using the combinations of primers of the present invention. All the combinations of primers in Table 10 do not amplify the DNAs of pathogenic bacteria other than EHEC (VTEC). It can therefore be concluded that the oligonucleotide primers of the present invention selectively react with the DNAs of the bacteria having the VT2 gene.

Example 7

Detection of EHEC (VTEC) Having the VT1 Gene, the VT2 Gene or a Variant Gene of the VT2 Gene

[Experiment 1]

Preparation of Specimens

The same procedure as used in Experiment 1 of Example 1 is followed.

Synthesis of Primers

As primers for amplifying the VT1 gene, the VT2 gene or a variant gene of VT2 (VT2vha, VT2vhb or VT2vp1), the above-described oligonucleotides SEQ ID NO:16, SEQ ID NO:17 and SEQ ID NO:18 are selected. These oligonucleotides are chemically synthesized by the same method as in Experiment 1 of Example 1.

PCR

PCR is carried out under the same reaction conditions as in Example 1 except that any one of the following oligonucleotide combinations is used:

Primer (1)+primer (2)=

Oligonucleotide SEQ ID NO:16+Oligonucleotide SEQ ID NO:18; and

Oligonucleotide SEQ ID NO:17+Oligonucleotide SEQ ID NO:18.

Detection

Agarose Gel Electrophoresis

The same procedure as in Experiment 1 of Example 1 is followed.

Colony Hybridization Test

The same procedures as in Experiment 1 of Example 1 are followed.

Results

The base sequences of the VT1 gene, the VT2 gene, the VT2vha gene, the VT2vhb gene and the VT2vp1 gene of EHEC(VTEC) have already been determined. Therefore, the length of the nucleotide fragments amplified by PCR using the oligonucleotides of the present invention as primers can easily be estimated. Specifically, when the oligonucleotides SEQ ID NO:16 and SEQ ID NO:18 of the present invention are used in combination, a nucleotide fragment of 495 bases (or a nucleotide duplex of 495 base pairs) should be amplified. When this estimation accords with the length of the amplified nucleotide fragment, it is judged that PCR using the combination of primers accurately amplifies the target region in the VT1 gene, the VT2 gene, the VT2vha gene, the VT2vhb gene or the VT2vp1 gene, and that some bacterial strains in the specimen have any one of these genes. The results obtained from the agarose gel electrophoresis and from the colony hybridization test with 320 test strains are given in Table 12. PCR using the primers of the present invention amplifies only DNA of the strains which give the positive result for the VT1 gene or the VT2 gene, showing no amplification of the DNA of the strains negative for these genes. This indicates that PCR using the primers of the present invention is capable of accurately amplifying the VT1 gene or the VT2 gene (including its variant genes) and that EHEC(VTEC) having the VT1 gene or the VT2 gene or the both can be detected with high accuracy by using the oligonucleotides of the present invention.

TABLE 12

Accuracy of the primers

|  |  |  |  | Results of colony hybridization test | |
|---|---|---|---|---|---|
|  |  |  |  | Positive for VT 1 or VT 2 gene | Negative for both VT 1 and VT 2 genes |
| Results of PCR | Combination of primers | 16 + 18* | Positive | 277 | 0 |
|  |  |  | Negative | 0 | 43 |
|  |  | 17 + 18* | Positive | 277 | 0 |
|  |  |  | Negative | 0 | 43 |

Note) *Numerals refer to SEQ ID NOs.

[Experiment 2]

To determine whether the results obtained in Experiment 1 are specific to EHEC (VTEC) having the VT1 gene or the VT2 gene, DNAs of clinically important pathogenic bacteria other than EHEC (VTEC) are examined with the primers of the present invention. The same procedure as used in Experiment 2 of Example 5 is followed.

Results

Table 10 shows the results from the test using the combinations of the primers of the present invention. PCR using the combinations of the primers does not amplify DNAs of any other strains than EHEC (VTEC) except for the DNA of a certain type of Shigella species (*Shigella dysenteriae* type I).

It is well known that differentiation between EHEC (VTEC) and *Shigella dysenteriae* is impossible only by detecting the VT1 gene because not only EHEC (VTEC) but also Shigella dysenteriae has the VT1 gene. It can therefore be concluded that the oligonucleotide primers of the present invention selectively react with the DNAs of the bacteria having the VT1 gene or the VT2 gene.

Example 8

Detection of *Staphylococcus aureus* Having the TSST-1 Gene

[Experiment 1]

Preparation of Specimens

A total of 343 strains of *Staphylococcus aureus* are used. These strains are derived from food poisoning cases and the environment, and isolated from sources such as diarrheal stool, vomit and food. Each strain is inoculated to a brain heart infusion medium (manufactured by BBL Co., Ltd.), and subjected to overnight shaking culture at 37° C. under aerobic conditions. Each culture broth is diluted 10 folds with TE buffer, and heated at 95° C. for 5 minutes, followed by centrifugation at 5000 rpm for 1 minute; the supernatants are used as specimens.

Synthesis of Primers

As primers for amplifying the TSST-1 gene of *Staphylococcus aureus*, the above-described oligonucleotides SEQ ID NO:19 to SEQ ID NO:22 are selected based upon the known base sequences of the TSST-1 gene of *Staphylococcus aureus* [Blomster-Hautamaa et al., J. Biol. chem., 26, 15783–15786 (1986)], and chemically synthesized by the same method as in Experiment 1 of Example 1.

PCR

To 3 μl of the above-described specimen solution, 16.05 μl of sterile distilled water, 3 μl of 10×reaction buffer, 4.8 μl of dNTP solution, 1.0 μl of primer (1), 1.0 μl of primer (2), and 0.15 μl of a thermostable DNA polymerase are added to prepare 30 μl of a reaction mixture. This reaction mixture is overlaid with 50 μl of mineral oil (produced by SIGMA). The contents of the solutions used and the primers (1) and (2) are as follows:

10×reaction buffer: 500 mM KCl, 100 mM Tris-HCl, pH 8.3, 15 mM $MgCl_2$, 0.1% (w/v) gelatin.

dNTP solution: A mixture of dATP, dCTP, dGTP and dTTP, each having a final concentration of 1.25 mM.

Primers: Aqueous solution of the above-described chemically synthesized purified oligonucleotides (concentration, 3.75 OD/ml) is prepared. Any one of the following oligonucleotide combinations is used:

Primer (1)+primer (2)=

Oligonucleotide SEQ ID NO:20+Oligonucleotide SEQ ID NO:21

Oligonucleotide SEQ ID NO:19+Oligonucleotide SEQ ID NO:22 and

Oligonucleotide SEQ ID NO:20+Oligonucleotide SEQ ID NO:22

Thermostable DNA polymerase: Taq DNA polymerase (5 unit/ml; produced by Perkin Elmer Cetus).

The reaction conditions are as follows:

Thermal denaturation: 94° C. for 1 minute.
Annealing: 55° C. for 1 minute.
Polymerization: 72° C. for 1 minute.

The cycle of thermal denaturation, primer annealing and polymerization (5.7 minutes) is repeated for 35 cycles (entire time, about 3 hours). This procedure is performed using a DNA thermal cycler (produced by Perkin Elmer Cetus) in which the above reaction conditions are programmed.

Detection

Agarose Gel Electrophoresis

The same procedure as in Example 1 is followed.

Reversed Passive Latex Agglutination (RPLA) Test

A commercially available RPLA kit for detection of TSST-1 of *Staphylococcus aureus* (TST-RPLA "SEIKEN" produced by DENKA SEIKEN) is purchased. Specimens are prepared and tested according to the instruction manual attached except that the preparation of specimens is partially modified in order for the test strains to produce sufficient amount of its enterotoxin. That is, the brain heart infusion is changed to the one produced by BBL Co., Ltd.

Results

Table 13 shows the comparison of the results of the PCR method of the present invention with the results of the TST-RPLA which are conventionally used. The data indicates that the detection method of the present invention can detect the TSST-1 gene of *Staphylococcus aureus* with a sensitivity comparable to or higher than the conventional TST-RPLA method. The data in Table 13 show that 17 of the 18 PCR positive strains are also positive by RPLA, and that 325 strains are negative by both PCR and RPLA. That is, except one strain which is positive by PCR and negative by RPLA, the same results are obtained by PCR and by RPLA. The strain, for which the result.by PCR and that by RPLA disaccord with each other, is tested by the Southern blot hybridization, and is confirmed to be positive for the TSST-1 gene.

TABLE 13

Comparison of PCR and TST-RPLA

|  | P C R positive | P C R negative |
|---|---|---|
| T S T-R P L A positive | 17 | 0 |
| T S T-R P L A negative | 1 | 325 |

Figure 1:
FIG. 1 is the pattern of the electrophoresis of the amplified DNA fragments on an agarose gel to evaluate the sensitivity of the detection method of the present invention for the TSST-1 gene of *Staphylococcus aureus*, wherein numerals 1 to 9 refer to the number of DNA copies used in the polymerase chain reaction (hereinafter simply referred to as PCR): 1 means $10^7$ copies; 2, $10^6$ copies; 3, $10^5$ copies; 4, $10^4$ copies; 5, $10^3$ copies; 6, $10^2$ copies; 7, 10 copies; 8, 1 copy; and 9, no DNA.

FIG. 1 shows the results of the sensitivity test for the PCR primers of the present invention by electrophoresis. In the figure, numerals 1 to 9 indicate the number of DNA copies used in the PCR reaction: 1 indicates $10^7$ copies; 2, $10^6$ copies; 3, $10^5$ copies; 4, $10^4$ copies; 5, $10^3$ copies; 6, $10^2$ copies; 7, 10 copies; 8, 1 copy; and 9, absence of DNA. From this figure, it is obvious that only 10 copies of DNA can be detected by the method of the present invention.

[Experiment 2]

To determine whether the results obtained in Experiment 1 are specific to *Staphylococcus aureus* having the TSST-1 gene, DNAs of other clinically important pathogenic bacteria are examined with the primers of the present invention. The same procedure as used in Experiment 1 is followed, except for the method of preparation of specimens.

Preparation of Specimens

Each strain listed in Table 14 is treated in the same manner as in Experiment 2 of Example 5.

Results

Table 14 shows the results of the test using the primers of the present invention. PCR using the primers does not amplify any DNAs of other strains including those causative for food poisoning. It can therefore be concluded that the oligonucleotide primers of the present invention selectively react with the DNA of *Staphylococcus aureus* having the TSST-1 gene. The similar results are obtained with the other combinations of the primers of the present invention which are not listed in Table 14.

TABLE 14

|  |  |  | Combination of primers | | |
|---|---|---|---|---|---|
| No | Strains |  | 20 + 21* | 19 + 22* | 20 + 22* |
| 1 | *Bacillus cereus* | ATCC 14579 | − | − | − |
| 2 | *Bacillus subtilis* | JCM 1455 | − | − | − |
| 3 | *Staphylococcus aureus* | JCM 2413 | − | − | − |
| 4 | *Staphylococcus epidermidis* | JCM 2414 | − | − | − |
| 5 | *Salmonella typhimurium* | IFO 12529 | − | − | − |
| 6 | *Salmonella enteritidis* | IFO 3163 | − | − | − |
| 7 | *Clostridium perfringens* | ATCC 12917 | − | − | − |
| 8 | *Vibrio cholerae* | ATCC 25872 | − | − | − |
| 9 | *Vibrio cholerae* type Ogawa | ATCC 9458 | − | − | − |
| 10 | *Vibrio cholerae* type Inaba | ATCC 9459 | − | − | − |
| 11 | *Vibrio fluvialis* | JCM 3752 | − | − | − |
| 12 | *Campylobacter jejuni* | JCM 2013 | − | − | − |
| 13 | *Campylobacter coli* | JCM 2529 | − | − | − |
| 14 | *Eschericia coli* | JCM 1548 | − | − | − |
| 15 | *Yersinia enterocolitica* | ATCC 5610 | − | − | − |
| 16 | *Shigella dysenteriae* | ATCC 3361 | − | − | − |
| 17 | *Shigella flexneri* | ATCC 29903 | − | − | − |
| 18 | *Shigella sonnei* | ATCC 29930 | − | − | − |
| 19 | *Bacteroides fragilis* | ATCC 23745 | − | − | − |
| 20 | *Bacteroides vulgatus* | JCM 5826 | − | − | − |
| 21 | *Enterococcus faecalis* | JCM 5803 | − | − | − |
| 22 | *Klebsiella pneumoniae* | JCM 1662 | − | − | − |
| 23 | *Protaus vulgaris* | JCM 1688 | − | − | − |
| 24 | *Citrobacter freundii* | ATCC 33128 | − | − | − |
| 25 | *Streptococcus pyogenes* | ATCC 12344 | − | − | − |
| 26 | *Streptococcus pneumoniae* | ATCC 33400 | − | − | − |
| 27 | *Haemophilus influenzae* | ATCC 33391 | − | − | − |
| 28 | *Proteus mirabilis* | ATCC 29906 | − | − | − |
| 29 | *Neisseria gonorrhoeae* | ATCC 19424 | − | − | − |
| 30 | *Neisseria meningitidis* | ATCC 13077 | − | − | − |
| 31 | *Listeria monocytogenes* | ATCC 15313 | − | − | − |
| 32 | *Lactobacillus acidophilus* | JCM 1132 | − | − | − |
| 33 | *Bifidobacterium adolescentis* | JCM 1275 | − | − | − |
| 34 | *Fusobacterium nucleatum* | ATCC 25585 | − | − | − |
| 35 | *Propionibacierium acnes* | ATCC 5918 | − | − | − |
| 36 | *Veillonella atypica* | ATCC 17744 | − | − | − |
| 37 | *Pseudomonas aeruginosa* | IFC 12689 | − | − | − |
| 38 | *Corynebacterium diphtheriae* | JCM 1310 | − | − | − |
| 39 | *Peptostreptococcus anaerobius* | ATCC 27337 | − | − | − |

Note)
*Numerals refer to SEQ ID NOs.

Example 9

Detection of *Vibrio cholerae* Having the ctx Gene

[Experiment 1]

Preparation of Specimens

The same procedure as used in Example 1 is followed except that 622 strains of *Vibrio cholerae* are used. These strains are isolated from patients with cholera, marine products (shrimp, snapping turtle), water collected from river, harbor, etc. Serotype, biotype, the numbers of the strains are listed in Table 15.

TABLE 15

Type and sources of Vibrio cholerae

| Serotype | Biotype | Patients | Food | Environment water | Total |
|---|---|---|---|---|---|
| O 1 Ogawa | El Tor | 148 | 125 | 71 | 344 |
| Inaba | | 16 | 27 | 26 | 69 |
| Ogawa | Asia | 15 | 0 | 0 | 15 |
| Inaba | (classical) | 26 | 0 | 0 | 26 |
| non O 1 | — | 168 | 0 | 0 | 168 |
| | Total | 373 | 152 | 97 | 622 |

Synthesis of Primers

As primers for amplifying the ctx gene of *Vibrio cholerae*, the above-described oligonucleotides SEQ ID NO:23 to SEQ ID NO:26 are selected based upon the known base sequences of the ctx gene of *Vibrio cholerae* [Lockman, H. and J. B. Kaper: J. Biol. Chem., 258, 13722–13726 (1983)], and chemically synthesized by the same method as in Experiment 1 of Example 1.

PCR

PCR is carried out under the same reaction conditions as in Example 1 except that any one of the following oligonucleotide combinations is used:

Primer (1)+primer (2)=

Oligonucleotide SEQ ID NO:23+Oligonucleotide SEQ ID NO:25; and

Oligonucleotide SEQ ID NO:24+Oligonucleotide SEQ ID NO:26.

Detection

Agarose Gel Electrophoresis

To detect the amplified nucleotide fragments in the reaction solution, agarose gel electrophoresis is carried out by the same procedure as in Example 1.

Colony Hybridization Test

A colony hybridization test is carried out using an polynucleotide probe specific to the ctx gene [Kaper, J. B., J. G. Morris, Jr., and N. Nishibuchi (1988), DNA probes for pathogenic Vibrio species, 65–77. In F. C. Tenover (ed.), DNA probes for infectious diseases. CRC Press, Inc., Boca Raton, Fla.] according to the procedure described by Grunstein [Grunstein, M. and Hogness, D., Proc. Natl. Acad. Sci., 72, 3961(1975)].

Results

The base sequences of the ctx gene of *Vibrio cholerae* have already been determined. Therefore, the length of the nucleotide fragments amplified by PCR using the oligonucleotides of the present invention as primers can easily be estimated. Specifically, when the oligonucleotides SEQ ID NO: 23 and SEQ ID NO:25 of the present invention are used in combination, a nucleotide fragment of 169 bases (or a nucleotide duplex of 169 base pairs) should be amplified. The combination of SEQ ID NO: 24 and SEQ ID NO:26 should amplify a nucleotide fragment of 307 bases (or a nucleotide duplex of 307 base pairs). When the estimated length of nucleotide accords with the length of the amplified nucleotide fragments, it is judged that PCR using the combination of primers accurately amplifies the target region in the ctx gene, and that the bacterial strain in the specimen has the ctx gene. The results obtained from the agarose gel electrophoresis and from the colony hybridization test with 662 test strains are given in Table 16. PCR using the primers of the present invention amplifies only DNAs of the strains which give a result positive for the ctx gene in the colony hybridization test, showing no amplification of the DNA of the ctx gene negative strains. This indicates that PCR using the primers of the present invention is capable of accurately amplifying the ctx gene and that *Vibrio cholerae* having the ctx gene can be detected with high accuracy by using the oligonucleotides of the present invention. Table 16 shows the result obtained with oligonucleotides SEQ ID NO: 24 and SEQ ID NO: 26. The combination of SEQ ID NO:23 and SEQ ID NO:25 also gives a similar result.

TABLE 16

Accuracy of primer combination of SEQ ID NO:24 and SEQ ID NO:26.

| | Results of colony hybridization test | |
|---|---|---|
| | ctx gene positive | ctx gene negative |
| Results of PCR | | |
| positive | 412 | 0 |
| negative | 0 | 210 |

Figure 2:
FIG. 2 is the pattern of the agarose gel electrophoresis of the nucleotide fragments amplified by PCR to evaluate the specificity of the detection method of the present invention for the ctx gene of *Vibrio cholerae*, wherein M indicates the molecular weight marker and lanes 1–13 indicate the template DNA solutions containing heat extract of the following strains.

FIG. 2 shows that PCR using the combinations of the primers of the present invention can accurately detect the ctx gene irrespective of the source, serological type and biological type of the strains. Heat extracts of the following strains are used as the template DNA solutions:

Lanes 1 to 3: *Vibrio cholerae* (El Tor—Ogawa type, the ctx gene positive strain)

Lanes 4 to 6: *Vibrio cholerae* (El Tor—Inaba type, the ctx gene positive strain)

Lane 7: *Vibrio cholerae* (Classical—Ogawa type, the ctx gene positive strain)

Lane 8: *Vibrio cholerae* (Classical—Inaba type, the ctx gene positive strain)

Lanes 9 to 10: *Vibrio cholerae* (non-O1, the ctx gene positive strain)

Lane 11: *Vibrio cholerae* (El Tor—Ogawa type, the ctx gene negative strain)

Lane 12: *Vibrio cholerae* (El Tor—Inaba type, the ctx gene negative strain)

Lane 13: Enterotoxigenic *Escherichia coli* (Thermolabile enterotoxin gene positive strain)

[Experiment 2]

To determine whether the results obtained in Experiment 1 are specific to *Vibrio cholerae* having the ctx gene, the genes of other clinically important pathogenic bacteria are examined with the method of the present invention. The same procedure as used in Experiment 1 is followed, except for the method of preparation of specimens.

Preparation of Specimens

Each strain listed in Table 17 is treated in the same manner as in Experiment 2 of Example 5.

Results

Table 17 shows the results of the test using a combination of primers of the present invention. PCR using the primers does not amplify DNAs of any other pathogenic strains tested. It can therefore be concluded that the oligonucleotide primers of the present invention selectively react with the DNAs of *Vibrio cholerae* having the ctx gene. Similar results are obtained also for the other combination of primers of the present invention which is not listed in Table 17.

TABLE 17

Reactivity with DNA of bacteria other than *Vibrio cholerae*

| No | Strains | | +/−* |
|---|---|---|---|
| 1 | *Bacillus cereus* | ATCC 14579 | − |
| 2 | *B. subtilis* | JCM 1465 | − |
| 3 | *Staphylococcus aureus* | JCM 2413 | − |
| 4 | *S. epidermidis* | JCM 2414 | − |
| 5 | *Salmonella typhimurium* | IFO 12529 | − |
| 6 | *S. enteritidis* | IFO 3163 | − |
| 7 | *Clostridium perfringens* | ATCC 12917 | − |
| 8 | *Vibrio fluvialis* | JCM 3752 | − |
| 9 | *Campylobacter jejuni* | JCM 2013 | − |
| 10 | *C. coli* | JCM 2529 | − |
| 11 | *Escherichia coli* | JCM 1649 | − |
| 12 | *Yersinia enterocolitica* | ATCC 9610 | − |
| 13 | *Shigella dysenteriae* | ATCC 9361 | − |
| 14 | *S. flexneri* | ATCC 29903 | − |
| 15 | *S. sonnei* | ATCC 29930 | − |
| 16 | *Bacteroides fragilis* | ATCC 23745 | − |
| 17 | *B. vulgatus* | JCM 5826 | − |
| 18 | *Enterococcus faecalis* | JCM 5803 | − |
| 19 | *Klebsiella pneumoniae* | JCM 1662 | − |
| 20 | *Proteus vulgaris* | JCM 1668 | − |
| 21 | *Citrobacter freundii* | ATCC 33128 | − |
| 22 | *Streptococcus pyogenes* | ATCC 12344 | − |
| 23 | *S. pneumoniae* | ATCC 33400 | − |
| 24 | *Haemophilus influenzae* | ATCC 33391 | − |
| 25 | *Proteus mirabilis* | ATCC 29906 | − |
| 26 | *Neisseria gonorrhoeae* | ATCC 19424 | − |
| 27 | *N. meningitidis* | ATCC 13077 | − |
| 28 | *Listeria monocytogenes* | ATCC 15313 | − |
| 29 | *Lactobacillus acidophilus* | JCM 1132 | − |
| 30 | *Bifidobacterium adolescentis* | JCM 1275 | − |
| 31 | *Fusobacterium nucleatum* | ATCC 2558 | − |
| 32 | *Propionibacterium acnes* | ATCC 6919 | − |
| 33 | *Veillonella atypica* | ATCC 17744 | − |
| 34 | *Pseudomonas aeruginosa* | IFO 12689 | − |
| 35 | *Corynebacterium diphtheriae* | JCM 1310 | − |
| 36 | *Peptostreptococcus anaerobius* | ATCC 27337 | − |
| 37 | Human placental DNA | | − |

Note)
*+reactive
−nonreactive

Example 10

Detection of *Clostridium perfringens* Having the Enterotoxin Gene

[Experiment 1]

Preparation of Specimens

The strains of *Clostridium perfringens* used are 11 strains isolated from patients, and provided by institutes where each strain is stored. Each strain is inoculated to GAM broth (manufactured by Nissui Pharmaceutical Co., Ltd.) and subjected to overnight shaking culture at 37° C. under anaerobic conditions. Each culture broth is diluted 10 folds with 10 mM Tris-HCl buffer, pH 7.5, and heated at 95° C. for 10 minutes, followed by centrifugation to use the supernatant as a specimen.

Synthesis of Primers

As primers for amplifying the enterotoxin gene of *Clostridium perfringens*, the above-described oligonucleotides SEQ ID NO:27 to SEQ ID NO:35 are selected based upon the known base sequences of the enterotoxin gene of *Clostridium perfringens* [Maruke van Damme-Jongsten, Antonie van Leeuwenhoek, 56, 181–190(1989)], and chemically synthesized by the same method as in Experiment 1 of Example 1.

PCR

PCR is carried out under the same reaction conditions as in Example 1 except that any one of the following oligonucleotide combinations is used:

Primer (1)+primer (2)=

Oligonucleotide SEQ ID NO:27+Oligonucleotide SEQ ID NO:32;

Oligonucleotide SEQ ID NO:28+Oligonucleotide SEQ ID NO:33;

Oligonucleotide SEQ ID NO:29+Oligonucleotide SEQ ID NO:33;

Oligonucleotide SEQ ID NO:30+Oligonucleotide SEQ ID NO:34; and

Oligonucleotide SEQ ID NO:31+Oligonucleotide SEQ ID NO:35.

Detection

Agarose Gel Electrophoresis

To detect the amplified nucleotide fragments in the reaction solution, agarose gel electrophoresis is carried out by the same procedure as in Example 1.

FIG. 3 shows a part of the electrophoretic results. The upper part of the figure shows the results with Oligonucleotide SEQ ID NO:28+Oligonucleotide SEQ ID NO:33; and the lower part, the results with Oligonucleotide SEQ ID NO:29+Oligonucleotide SEQ ID NO:33. In the figure, M indicates the molecular weight marker; and lanes 1 to 13 respectively indicate ATCC 12925(lane 1), ATCC 12924 (lane 2), ATCC 12922(lane 3), ATCC 12920(lane 4), ATCC 12916(lane 5), ATCC 12915(lane 6), ATCC 12918(lane 7), ATCC 12919(lane 8), ATCC 12921(lane 9), JCM 1296(lane 10), JCM 1416(lane 11), JCM 1382(lane 12), and TE (negative control, lane 13).

Southern Blot Hybridization Test

A southern blot hybridization test is carried out usihg an oligonucleotide probe specific to the enterotoxin gene of *Clostridium perfringens* according to the method described by Tada et al. [Tada, J. et al. Mol. Cell. Probe., 6, 477 (1992)].

Reversed Passive Latex Agglutination (RPLA) Test

A commercially available RPLA kit for detection of *Clostridium perfringens* enterotoxin (PET-RPLA "SEIKEN" produced by DENKA SEIKEN) is purchased. Specimens are prepared and tested according to the instruction manual attached.

Results

The base sequences of the enterotoxin gene of *Clostridium perfringens* have already been determined. Therefore, the length of the nucleotide fragments amplified by PCR using the oligonucleotides of the present invention as primers can easily be estimated. Specifically, when the oligonucleotides SEQ ID NO:27 and SEQ ID NO:32 of the present invention are used in combination, a nucleotide fragment of 473 bases (or a nucleotide duplex of 473 base pairs) should be amplified. When the estimated length accords with the length of the amplified nucleotide fragment, it is judged that PCR using the combination of the primers accurately amplifies the target region in the enterotoxin gene, and that the bacterial strain in the specimen has the enterotoxin gene. The results obtained from the agarose gel electrophoresis and from the RPLA test with the 11 test strains are given in Table 18.

TABLE 18

| | | Results of RFLA | Combination of primers and length of amplified DNA (No. of b.p.)* | | | | |
|---|---|---|---|---|---|---|---|
| Strains | | | 27 + 32** 473 | 28 + 33** 456 | 29 + 33** 421 | 30 + 34** 267 | 31 + 35** 156 |
| 01 Clostridium perfringens | ATCC 12915 | +*** | + | + | + | + | + |
| 02 Clostridium perfringens | ATCC 12916 | + | + | + | + | + | + |
| 03 Clostridium perfringens | ATCC 12917 | + | + | + | + | + | + |
| 04 Clostridium perfringens | ATCC 12918 | + | + | + | + | + | + |
| 05 Clostridium perfringens | ATCC 12919 | − | − | − | − | − | − |
| 06 Clostridium perfringens | ATCC 12920 | + | + | + | + | + | + |
| 07 Clostridium perfringens | ATCC 12921 | − | − | − | − | − | − |
| 08 Clostridium perfringens | ATCC 12922 | + | + | + | + | + | + |
| 09 Clostridium perfringens | ATCC 12924 | + | + | + | + | + | + |
| 10 Clostridium perfringens | ATCC 12925 | + | + | + | + | + | + |
| 11 Clostridium perfringens | JCM 3816 | − | − | − | − | − | − |

Note
*+DNA of estimated length is amplified.
−DNA of any length is not amplified.
**Numerals refer to SEQ ID NOs.
***+Agglutination: Enterotoxin is produced.
−No agglutination: Enterotoxin is not produced.

In the Southern blot hybridization test, it is confirmed that the nucleotide fragments amplified with a combination of the primers of the present invention is a part of the enterotoxin gene sequences. The results are shown in FIG. 4. FIG. 4 corresponds to FIG. 3. In the figure, M indicates the molecular weight marker; and lanes 1 to 13 respectively indicate ATCC 12925(lane 1), ATCC 12924(lane 2), ATCC 12922(lane 3), ATCC 12920(lane 4), ATCC 12916(lane 5), ATCC 12915(lane 6), ATCC 12918(lane 7), ATCC 12919 (lane 8), ATCC 12921(lane 9), JCM 1296(lane 10), JCM 1416(lane 11), JCM 1382(lane 12), and TE (negative control, lane 13).

These results indicate that PCR using the primers of the present invention is capable of accurately amplifying the enterotoxin gene in PCR and that Clostridium perfringens having the enterotoxin gene can be detected with high accuracy by using the oligonucleotides of the present invention.

[Experiment 2]

To determine whether the results obtained in Experiment 1 are specific to Clostridium perfringens having the enterotoxin gene, the reactivity of the primers of the present invention with the DNAs of other Clostridium species and other clinically important pathogenic bacteria is examined. The same procedure as used in Experiment 1 is followed, except for the method of preparation of specimens.

Preparation of Specimens

Each strain listed in Tables 19 and 20 is treated in the same manner as in Experiment 2 of Example 5.

Results

Tables 19 and 20 show the results of the test using some of the combinations of primers of the present invention. All the combinations of the primers listed in the tables do not show any amplification of DNAs of other strains including pathogenic strains in PCR. It can therefore be concluded that the oligonucleotide primers of the present invention selectively react with the enterotoxin gene of Clostridium perfringens.

TABLE 19

| | | Combination of primers and length of amplified DNA (No. of b.p.)* | | | | |
|---|---|---|---|---|---|---|
| Strains | | 27 + 32** 473 | 28 + 33** 456 | 29 + 33** 421 | 30 + 34** 267 | 31 + 35** 156 |
| 01 Clostridium absonum | ATCC 27555 | − | − | − | − | − |
| 02 Clostridium barati | JCM 1382 | − | − | − | − | − |
| 03 Clostridium bifermentans | ATCC 638 | − | − | − | − | − |
| 04 Clostridium butyricum | JCM 1391 | − | − | − | − | − |
| 05 Clostridium difficile | JCM 1296 | − | − | − | − | − |
| 06 Clostridium fallax | JCM 1398 | − | − | − | − | − |
| 07 Clostridium histolyticum | JCM 1403 | − | − | − | − | − |
| 08 Clostridium novyi | JCM 1406 | − | − | − | − | − |
| 09 Clostridium sordellii | JCM 3814 | − | − | − | − | − |
| 10 Clostridium sphenoides | JCM 1415 | − | − | − | − | − |
| 11 Clostridium spiroforme | JCM 1432 | − | − | − | − | − |
| 12 Clostridium sporogenes | JCM 1416 | − | − | − | − | − |
| 13 Clostridium tertiium | JCM 6289 | − | − | − | − | − |

Note)
*+DNA of estimated length is amplified.
−DNA of any length is not amplified.
**Numerals refer to SEQ ID NOs.

TABLE 20

| | | Combination of primers and length of amplified DNA (No. of b.p.)* | | | | |
|---|---|---|---|---|---|---|
| Strains | | 27 + 32<br>473 | 28 + 33<br>456 | 29 + 33<br>421 | 30 + 34<br>267 | 31 + 35**<br>156 |
| 01 Vibrio cholerae | ATCC 25872 | – | – | – | – | – |
| 02 Vibrio cholerae type Ogawa | ATCC 9458 | – | – | – | – | – |
| 03 Vibrio cholerae type Inaba | ATCC 9459 | – | – | – | – | – |
| 04 Vibrio fluviatis | JCM 3752 | – | – | – | – | – |
| 05 Vibrio metschnikovii | ATCC 7708 | – | – | – | – | – |
| 06 Vibrio mimicus | ATCC 33653 | – | – | – | – | – |
| 07 Bacillus cereus | ATCC 14579 | – | – | – | – | – |
| 08 Bacillus subtilis | JCM 1465 | – | – | – | – | – |
| 09 Staphylococcus aureus | JCM 2413 | – | – | – | – | – |
| 1o Staphylococcus epidermidis | JCM 2414 | – | – | – | – | – |
| 11 Salmonella typhimurium | IFO 12529 | – | – | – | – | – |
| 12 Salmonella enteritidis | IFO 3163 | – | – | – | – | – |
| 13 Campylobacter jejuni | JCM 2013 | – | – | – | – | – |
| 14 Campylobacter coli | JCM 2529 | – | – | – | – | – |
| 15 Escherichia coli | JCM 1649 | – | – | – | – | – |
| 16 Yersinia enterocolitica | ATCC 9610 | – | – | – | – | – |
| 17 Shigella dysenteriae | ATCC 9361 | – | – | – | – | – |
| 18 Shigella flexneri | ATCC 29903 | – | – | – | – | – |
| 19 Shigella sonnei | ATCC 29930 | – | – | – | – | – |
| 20 Bacteroides fragilis | ATCC 23745 | – | – | – | – | – |
| 21 Bacteroides vulgatus | JCM 5826 | – | – | – | – | – |
| 22 Enterococcus faecalis | JCM 5803 | – | – | – | – | – |
| 23 Klebsiella pneumoniae | JCM 1662 | – | – | – | – | – |
| 24 Proteus mirabilis | ATCC 29906 | – | – | – | – | – |
| 25 Proteus vulgaris | JCM 1668 | – | – | – | – | – |
| 26 Citrobacter freundii | ATCC 33128 | – | – | – | – | – |
| 27 Streptococcus pyogenes | ATCC 12344 | – | – | – | – | – |
| 28 Streptococcus pneumoniae | ATCC 33400 | – | – | – | – | – |
| 29 Haemophilus influenzae | ATCC 33391 | – | – | – | – | – |
| 30 Neisseria gonorrhoeae | ATCC 19424 | – | – | – | – | – |
| 31 Neisseria meningitidis | ATCC 13077 | – | – | – | – | – |
| 32 Listeria monocytogenes | ATCC 15313 | – | – | – | – | – |
| 33 Lactobacillus acidophilus | JCM 1132 | – | – | – | – | – |
| 34 Bifidobacterium adolescentis | JCM 1275 | – | – | – | – | – |
| 35 Fusobacterium nucleatum | ATCC 25586 | – | – | – | – | – |
| 36 Propionibacterium acnes | ATCC 6919 | – | – | – | – | – |
| 37 Veillonella atypica | ATCC 17744 | – | – | – | – | – |
| 38 Pseudomonas aeruginosa | IFO 12689 | – | – | – | – | – |
| 39 Corynebacterium diphtheriae | JCM 1310 | – | – | – | – | – |
| 40 Peptostreptococcus anaerobius | ATCC 27337 | – | – | – | – | – |

Note)
*+DNA of estimated length is amplified.
–DNA of any length is not amplified.
**Numerals refer to SEQ ID NOs.

The agarose gel electrophoresis used in the above examples of the present invention can differentiate nucleotide fragments from one another which are different in length by 5–10 bases (base pairs) for nucleotide fragments of not more than 100 bases (base pairs), and by 10–20 bases (base pairs) for nucleotide fragments of 100–500 bases (base pairs). In addition, the use of other gel material such as acrylamide makes it possible to improve the precision in measuring the length of nucleotide fragment. Thus, the reliability of the selective detection of the target gene in the present invention can further be increased.

While the invention has been described in detail and with reference to specific embodiments thereof, it will be apparent to one skilled in the art that various changes and modifications can be made therein without departing from the spirit and scope thereof.

What is claimed is:

1. A kit for detection of a bacterial strain, comprising at least a pair of primers selected from the group consisting of oligonucleotides of SEQ ID NOS:12–18 and a synthetic oligonucleotide consisting of a nucleotide sequence complementary to the oligonucleotides of SEQ ID NOS:12–18, a thermostable DNA polymerase, and dNTP solutions.

2. A synthetic oligonucleotide selected from the group consisting of SEQ. ID NOS:12–18.

3. A synthetic oligonucleotide consisting of a nucleotide sequence that is the complement of the synthetic oligonucleotide of claim 2.

4. A method for detecting a bacterial strain of verocytotoxin-producing *Escherichia coli*, wherein the method comprises i) hybridizing a first primer to a single-stranded target DNA as a first template DNA present in a biological specimen and carrying out a primer extension reaction to give a first primer extension product;

ii) denaturing a resulting DNA duplex of said primer extension product and said first template DNA to separate the primer extension product from the template DNA, the first primer extension product functioning as a second template DNA for a second primer;

iii) hybridizing the second primer to said second template DNA and carrying out a primer extension reaction to give a second primer extension product;

iv) repeating a cycle of simultaneous primer extension reaction with the first and second primers, separation of the first and second primer extension products from the first and second templates, and hybridization of first and second primers to amplify a region of the target DNA, in the steps from (1) to (3), said primers being selected from the group consisting of an oligonucleotide of claim 1 and a synthetic oligonucleotide comprising a nucleotide sequence complementary to the synthetic oligonucleotide of claim 1; and v) detecting the region of the target DNA that has been amplified to determine whether a suspected bacterial strain is present in the biological specimen.

5. A method for detecting a bacterial strain of Verocytotoxin-producing *Escherichia coli*, the method comprises i) hybridizing a first primer to a single-stranded target DNA as a first template DNA present in a biological specimen and carrying out a primer extension reaction to give a first primer extension product;

ii) denaturing a resulting DNA duplex of said primer extension product and said first template DNA to separate the primer extension product from the template DNA, the first primer extension product functioning as a second template DNA for a second primer;

iii) hybridizing the second primer to said second template DNA and carrying out a primer extension reaction to give a second primer extension product;

iv) repeating a cycle of simultaneous primer extension reaction with the first and second primers, separation of the first and second primer extension products from the first and second templates, and hybridization of first and second primers to amplify a region of the target DNA, in the steps from (1) to (3), said primers being selected from the following oligonucleotide combinations:

a combination in which the first primer consisting of 10–30 bases comprising at least 10 consecutive bases of SEQ ID NO:12 and the second primer consisting of 10–30 bases comprising at least 10 consecutive bases of SEQ ID NO:13;

a combination in which the first primer consisting of 10–30 bases comprising at least 10 consecutive bases of SEQ ID NO:14 and the second primer consisting of 10–30 bases comprising at least 10 consecutive bases of SEQ ID NO:15;

a combination in which the first primer consisting of 10–30 bases comprising at least 10 consecutive bases of SEQ ID NO:16 and the second primer consisting of 10–30 bases comprising at least 10 consecutive bases of SEQ ID NO:18;

a combination in which the first primer consisting of 10–30 bases comprising at least 10 consecutive bases of SEQ ID NO:17 and the second primer consisting of 10–30 bases comprising at least 10 consecutive bases of SEQ ID NO:18; and v) detecting the region of the target DNA that has been amplified to determine whether a suspected bacterial strain is present in the biological specimen.

* * * * *

SEQUENCE LISTING (1) GENERAL INFORMATION:

(iii) NUMBER OF SEQUENCES: 35

(2) INFORMATION FOR SEQ ID NO:1:

```
    (i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Shigella dysenteriae
        (B) STRAIN: type 1

(xi) SEQUENCE DESCRIPTION: SEQ ID NO:1:

CAACACTGGA TGATCTCAG                                                  19

(2) INFORMATION FOR SEQ ID NO:2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Shigella dysenteriae
        (B) STRAIN: type 1

(xi) SEQUENCE DESCRIPTION: SEQ ID NO:2:

CCCCCTCAAC TGCTAATA                                                   18

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Shigella dysenteriae, Shigella flexneri,
            Shigella boydii and Shigella sonnei (xi) SEQUENCE DESCRIPTION: SEQ ID NO:3:

TGTATCACAG ATATGGCATG C                                               21

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO
```

(iv) ANTI-SENSE: NO (vi) ORIGINAL SOURCE:
             (A) ORGANISM: Shigella dysenteriae, Shigella flexneri,
                 Shigella boydii and Shigella sonnei (xi) SEQUENCE DESCRIPTION: SEQ ID NO:4:

TCCGGAGATT GTTCCATGTG                                                   20

(2) INFORMATION FOR SEQ ID NO:5:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Shigella dysenteriae, Shigella flexneri,
                 Shigella boydii and Shigella sonnei (xi) SEQUENCE DESCRIPTION: SEQ ID NO:5:

CAAGATTTAA CCTTCGTCAA CC                                                22

(2) INFORMATION FOR SEQ ID NO:6:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Shigella dysenteriae, Shigella flexneri,
                 Shigella boydii and Shigella sonnei (xi) SEQUENCE DESCRIPTION: SEQ ID NO:6:

AGTTCTCGGA TGCTATGCTC                                                   20

(2) INFORMATION FOR SEQ ID NO:7:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Salmonella spp.

(xi) SEQUENCE DESCRIPTION: SEQ ID NO:7:

CGCGGAGAGG GCGTCATT                                                     18

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Salmonella spp.

(xi) SEQUENCE DESCRIPTION: SEQ ID NO:8:

GCAACGACTC ATTAATTACC G        21

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Salmonella spp.

(xi) SEQUENCE DESCRIPTION: SEQ ID NO:9:

ATCTGGTCGC CGGGCTGA        18

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Salmonella spp.

(xi) SEQUENCE DESCRIPTION: SEQ ID NO:10:

GCATCGCGCA CACGGCTA        18

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO

```
        (vi) ORIGINAL SOURCE:
              (A) ORGANISM: Salmonella spp.

(xi) SEQUENCE DESCRIPTION: SEQ ID NO:11:

GGCGAGCAGT TTGTCTGTC                                                    19

(2) INFORMATION FOR SEQ ID NO:12:

(i) SEQUENCE CHARACTERISTICS:
              (A) LENGTH: 19 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: Escherichia coli (xi) SEQUENCE DESCRIPTION: SEQ ID NO:12:

CAACACTGGA TGATCTCAG                                                    19

(2) INFORMATION FOR SEQ ID NO:13:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: Escherichia coli (xi) SEQUENCE DESCRIPTION: SEQ ID NO:13:

CCCCCTCAAC TGCTAATA                                                     18

(2) INFORMATION FOR SEQ ID NO:14:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: Escherichia coli (xi) SEQUENCE DESCRIPTION: SEQ ID NO:14:

ATCAGTCGTC ACTCACTGGT                                                   20

(2) INFORMATION FOR SEQ ID NO:15:

(i) SEQUENCE CHARACTERISTICS:
              (A) LENGTH: 19 base pairs
```

(B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Escherichia coli (xi) SEQUENCE DESCRIPTION: SEQ ID NO:15:

CCAGTTATCT GACATTCTG                                                19

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Escherichia coli (xi) SEQUENCE DESCRIPTION: SEQ ID NO:16:

AGTTTACGTT AGACTTTTCG AC                                            22

(2) INFORMATION FOR SEQ ID NO:17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Escherichia coli (xi) SEQUENCE DESCRIPTION: SEQ ID NO:17:

CGGACAGTAG TTATACCAC                                                19

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Escherichia coli (xi) SEQUENCE DESCRIPTION: SEQ ID NO:18:

CTGCTGTCAC AGTGACAAA                                                    19

(2) INFORMATION FOR SEQ ID NO:19:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Staphylococcus aureus (xi) SEQUENCE DESCRIPTION: SEQ ID NO:19:

CCTTTAAAAG TTAAGGTTCA TG                                                22

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Staphylococcus aureus (xi) SEQUENCE DESCRIPTION: SEQ ID NO:20:

GGCCAAAGTT CGATAAAAAA C                                                 21

(2) INFORMATION FOR SEQ ID NO:21:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Staphylococcus aureus (xi) SEQUENCE DESCRIPTION: SEQ ID NO:21:

ATTTATAGGT GGTTTTTCAG TAT                                               23

(2) INFORMATION FOR SEQ ID NO:22:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Staphylococcus aureus (xi) SEQUENCE DESCRIPTION: SEQ ID NO:22:

CTGCTTCTAT AGTTTTTATT TCA                                              23

(2) INFORMATION FOR SEQ ID NO:23:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Vibrio cholerae (xi) SEQUENCE DESCRIPTION: SEQ ID NO:23:

TGATGAAATA AAGCAGTCAG GT                                               22

(2) INFORMATION FOR SEQ ID NO:24:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Vibrio cholerae (xi) SEQUENCE DESCRIPTION: SEQ ID NO:24:

ACAGAGTGAG TACTTTGACC                                                  20

(2) INFORMATION FOR SEQ ID NO:25:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Vibrio cholerae (xi) SEQUENCE DESCRIPTION: SEQ ID NO:25:

GGCACTTCTC AAACTAATTG AG                                               22

(2) INFORMATION FOR SEQ ID NO:26:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Vibrio cholerae (xi) SEQUENCE DESCRIPTION: SEQ ID NO:26:

ATACCATCCA TATATTTGGG AG                                          22

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Clostridium perfringens (xi) SEQUENCE DESCRIPTION: SEQ ID NO:27:

TCTGAGGATT TAAAAACACC                                             20

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Clostridium perfringens (xi) SEQUENCE DESCRIPTION: SEQ ID NO:28:

ACCCTCAGTA GGTTCAAGTC                                             20

(2) INFORMATION FOR SEQ ID NO:29:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO

```
        (iv) ANTI-SENSE: NO (vi) ORIGINAL SOURCE:
             (A) ORGANISM: Clostridium perfringens (xi) SEQUENCE DESCRIPTION: SEQ ID NO:29:

ATGAAACAGG TACCTTTAGC C                                              21

(2) INFORMATION FOR SEQ ID NO:30:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Clostridium perfringens (xi) SEQUENCE DESCRIPTION: SEQ ID NO:30:

GGTAATATCT CTGATGATGG AT                                             22

(2) INFORMATION FOR SEQ ID NO:31:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Clostridium perfringens (xi) SEQUENCE DESCRIPTION: SEQ ID NO:31:

TAACTCATAC CCTTGGACTC                                                20

(2) INFORMATION FOR SEQ ID NO:32:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Clostridium perfringens (xi) SEQUENCE DESCRIPTION: SEQ ID NO:32:

GAACCTTGAT CAATATTTCC                                                20

(2) INFORMATION FOR SEQ ID NO:33:

(i) SEQUENCE CHARACTERISTICS:
```

```
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Clostridium perfringens (xi) SEQUENCE DESCRIPTION: SEQ ID NO:33:

GTAGCAGCAG CTAAATCAAG G                                              21

(2) INFORMATION FOR SEQ ID NO:34:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Clostridium perfringens (xi) SEQUENCE DESCRIPTION: SEQ ID NO:34:

AGTCCAAGGG TATGAGTTAG                                                20

(2) INFORMATION FOR SEQ ID NO:35:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Clostridium perfringens (xi) SEQUENCE DESCRIPTION: SEQ ID NO:35:

CCATCACCTA AGGACTGTTC                                                20
```